United States Patent
Lee et al.

(10) Patent No.: US 11,634,685 B2
(45) Date of Patent: *Apr. 25, 2023

(54) SPORICHTHYACEAE MICROORGANISM AND USE THEREOF

(71) Applicant: Cosmax Co., Ltd., Hwaseong-si (KR)

(72) Inventors: Dong Geol Lee, Anyang-si (KR); Jin Ju Nam, Seongnam-si (KR); Min Ji Kim, Suwon-si (KR); Seung Hyun Kang, Seoul (KR); Youn Joon Kim, Seoul (KR)

(73) Assignee: COSMAX CO., LTD., Hwaseong-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/456,177

(22) Filed: Nov. 23, 2021

(65) Prior Publication Data

US 2022/0142912 A1 May 12, 2022

Related U.S. Application Data

(63) Continuation of application No. 15/759,688, filed as application No. PCT/KR2017/006741 on Jun. 27, 2017, now Pat. No. 11,261,421.

(30) Foreign Application Priority Data

| Jun. 27, 2016 | (KR) | 10-2016-0080231 |
| Nov. 22, 2016 | (KR) | 10-2016-0155981 |
| Jun. 16, 2017 | (KR) | 10-2017-0076819 |
| Jun. 16, 2017 | (KR) | 10-2017-0076820 |

(51) Int. Cl.
| C12N 1/20 | (2006.01) |
| A61P 17/02 | (2006.01) |
| A61P 29/00 | (2006.01) |
| A61P 17/04 | (2006.01) |
| A61K 8/99 | (2017.01) |
| A61K 35/74 | (2015.01) |
| A61Q 19/00 | (2006.01) |
| A61K 35/741 | (2015.01) |
| C12R 1/01 | (2006.01) |
| A61Q 19/08 | (2006.01) |

(52) U.S. Cl.
CPC .............. *C12N 1/205* (2021.05); *A61K 8/99* (2013.01); *A61K 35/74* (2013.01); *A61K 35/741* (2013.01); *A61P 17/02* (2018.01); *A61P 17/04* (2018.01); *A61P 29/00* (2018.01); *A61Q 19/00* (2013.01); *C12N 1/20* (2013.01); *A61Q 19/08* (2013.01); *C12R 2001/01* (2021.05); *Y02A 50/30* (2018.01)

(58) Field of Classification Search
None
See application file for complete search history.

(56) References Cited

U.S. PATENT DOCUMENTS

| 8,431,523 B2 | 4/2013 | Owen et al. |
| 8,586,541 B2 | 11/2013 | Owen et al. |
| 2019/0040475 A1 | 2/2019 | Lee et al. |

FOREIGN PATENT DOCUMENTS

| KR | 20090053752 A | 5/2009 |
| KR | 20100064516 A | 6/2010 |
| KR | 20140097340 A | 8/2014 |
| WO | 2010064762 A1 | 6/2010 |

OTHER PUBLICATIONS

Tamura, ("The Family Sporicthyacea" Chapter 41, The Prokaryotes—Actinobacteria, 2014, Springer Verlag, Heidelberg Germany, E. Rosenberg et al., editors, 883-887) Year: 2014).
Database EMBL [Online], "Epidermidibacterium keratini strain EPI-716S ribosomal RNA gene, partial sequence," (Sep. 15, 2016), XP002795722, retrieved from EBI accession No. EM_STD:KX755247, Database accession No. KX755247, Sep. 15, 2016, 1 page.
The extended European Search report dated Dec. 3, 2019, by the European Patent Office in corresponding European Patent Application No. 17820500.1-1120, 6 pages.
Notice of Allowance dated Sep. 6, 2018, by the Korean Patent Office in corresponding Korean Patent Application No. 10-2017-0076819, 7 pages.
Notice of Allowance dated Sep. 6, 2018, by the Korean Patent Office in corresponding Korean Patent Application No. 10-2017-0076820, 6 pages.
Carlsohn, M.R. et al., "*Fodinicola feengrottensis* gen. nov., sp. nov., an actinomycete isolated from a medieval mine", International Journal of Systematic and Evolutionary Microbiology, vol. 58, 2008, pp. 1529-1536.
Chen, Yi-Guang et al., "*Nocardiopsis terrae* sp. nov., a halophilic actinomycete isolated from saline soil", Antonie van Leeuwenhoek, vol. 98, 2010, pp. 31-38.
Lee, et al., "*Epidermidibacterium keratini* gen.nov., sp. nov., a member of the family Sporichthyaceae, isolated from keratin epidermis", International Journal of Systematic and Evolutionary Microbiology, vol. 68, No. 3, Mar. 1, 2018, pp. 745-750.
Lee, S.D., "*Motilibacter peucedani* gen. nov., sp. nov., isolated from rhizosphere soil", International Journal of Systematic and Evolutionary Microbiology, vol. 62, 2012, pp. 315-321.

(Continued)

*Primary Examiner* — Robert J Yamasaki
*Assistant Examiner* — Charles Zoltan Constantine
(74) *Attorney, Agent, or Firm* — Panitch Schwarze Belisario & Nadel LLP

(57) ABSTRACT

Provided is a microorganism of the genus *Epidermidibacterium* belonging to the family Sporichthyaceae, or a culture thereof, or a composition for preventing, improving, or treating skin conditions or inflammatory diseases including the same.

3 Claims, 14 Drawing Sheets

Specification includes a Sequence Listing.

(56) References Cited

OTHER PUBLICATIONS

International Search Report (PCT/ISA/210) dated Dec. 7, 2017, by the Korean Intellectual Property Office as the International Searching Authority for International Application No. PCT/KR2017/006741.
Written Opinion (PCT/ISA/237) dated Dec. 7, 2017, by Korean Intellectual Property Office as the International Searching Authority for International Application No. PCT/KR2017/006741.
Rainey, F.A. et al., "Sporichthya polymorpha represents a novel line of descent within the order Actinomycetales", FEMS Microbiology Letters, vol. 109, 1999, pp. 263-267.
Roudsari, et al., "Health Effects of Probiotics on the Skin", Critical Reviews in Food Science and Nutrition, vol. 55, No. 9, Jul. 29, 2015, pp. 1219-1240.
Tamura, T. et al., "*Sporichthya brevicatena* Sp. Nov", International Journal of Systematic Bacteriology, vol. 49, 1999, pp. 1779-1784.

FIG. 4

| # | Species | % | Accession |
|---|---|---|---|
| 5 | Staphylococcus sp. HB2 | 99 | AM263421 |
| 6 | Staphylococcus hominis strain CASM1N5 | 98 | JX435816 |
| 7 | Staphylococcus pasteuri | 100 | HQ793476 |
| 8 | Staphylococcus nepalensis | 98 | HQ717221 |
| 9 | Staphylococcus sp. C212 | 93 | HQ717231 |
| 10 | Staphylococcus warneri | 98 | GU361126 |
| 11 | Staphylococcaceae bacterium 11_Ne_0 | 85 | JX064805 |
| 12 | Uncultured Sphingomonas sp. | 86 | JX899974 |
| 13 | Uncultured Peptostreptococcaceae bacterium | 97 | EU289126 |
| 14 | Uncultured bacterium isolate | 84 | GQ289405 |
| 15 | Uncultured alpha proteobacterium | 99 | AJ318165 |
| 16 | Uncultured Sphingomonadaceae bacterium | 98 | GQ482942 |
| 17 | Staphylococcus sp. SDT18 | 99 | JX047449 |
| 18 | Staphylococcus nepalensis | 99 | KM500030 |
| 19 | Staphylococcus nepalensis | 99 | NM500030 |
| 20 | Uncultured bacterium | 99 | JF237797 |
| 21 | Uncultured bacterium | 88 | HQ760452 |
| 22 | Uncultured bacterium isolate | 93 | HQ113784 |
| 23 | Uncultured bacterium | 95 | JF174864 |
| 24 | Micrococcus sp. PP5 | 99 | KF554092 |
| 25 | Rhodococcus sp. BZN6 | 94 | AJ585369 |
| 26 | Brevibacterium sp. LC187 | 97 | JQ014375 |
| 27 | Uncultured bacterium | 98 | JX458387 |
| 28 | Uncultured bacterium | 96 | KF290510 |
| 29 | Staphylococcus sp. HB4 | 98 | AM263420 |
| 30 | Uncultured Aerococcus sp. isolate DGGE gel band Loc-2 | 83 | KC869974 |
| 31 | Staphylococcus epidermidis | 94 | CP000040 |
| 32 | Staphylococcus sp. HB2 | 99 | AM263421 |
| 33 | Uncultured bacterium isolate DGGE gel band A20 | 93 | HQ113784 |
| 34 | Uncultured bacterium clone g8b31 | 89 | KF612706 |
| 35 | Staphylococcus nepalensis | 97 | HQ717221 |
| 36 | Staphylococcus sp. CCAT14 | 92 | HG799946 |
| 37 | Uncultured Sphingomonas sp. clone EEMandiN | 86 | JX899974 |
| 38 | Uncultured bacterium clone ncd1823b01c1 | 99 | JF157350 | lermis A (rows 5–28)
lermis B (rows 29–38)

SPORICHTHYACEAE MICROORGANISM AND USE THEREOF

CROSS-REFERENCE TO RELATED APPLICATION

The present application is a continuation application of U.S. patent application Ser. No. 15/759,688 filed on Mar. 13, 2018, which is a U.S. National Stage application of International Patent Application No. PCT/KR2017/006741 filed on Jun. 27, 2017, and claims priority from Korean Patent Application Nos. 10-2016-0080231, 10-2016-0155981, 10-2017-0076819, and 10-2017-0076820, filed on Jun. 27, 2016, Nov. 22, 2016, Jun. 16, 2017, and Jun. 16, 2017, respectively, the disclosures of which are incorporated herein in their entirety by reference.

TECHNICAL FIELD

The present disclosure relates to a novel microorganism of the family Sporichthyaceae and use thereof.

A microorganism deposit was deposited on Jun. 8, 2016 in accordance with the Budapest Treaty on the International Recognition of the Deposit of Microorganisms for the Purposes of Patent Procedure. The deposit was identified as *Epidermidibacterium keratini* EPI-7 with an Accession number at the International Depository Authority of KCCM11843P. The deposit was submitted to the International Depositary Authority named Korean Culture Center of Microorganisms, with an address of Yurim B/D, 45, Hongje-nae-2ga-gil, Seodaemun-gu, Seoul 120-861, Republic of Korea.

BACKGROUND ART

The skin ecosystem provides diverse habitats for microorganisms, and a wide range of microorganisms occupy the skin ecosystem. It is known that these microorganisms have a symbiotic relationship with their human hosts and have many positive effects on the hosts. The skin forms a variety of habitats, such as invaginations, specified niches, etc., which help a wide range of microorganisms grow. The primary role of the skin is to form a physical barrier and to offer protection against a potential threat from the external environment and toxic substances. The skin is an interface with the external environment and is colonized by a diverse collection of microorganisms (fungi, bacteria, viruses, and small larvae). The microorganisms that are adapted to the niche they inhabit are selected according to selection of physical and chemical functions. In general, the skin is cool, acidic, and maintained in a dry state. Structurally, the epidermis plays a role in forming a physical barrier and resisting penetration by microorganisms and toxins while retaining moisture. The outermost layer of the epidermis is composed of the stratum corneum. The epidermis forms a so-called "brick and mortar" structure, the skin tissue undergoes continuous self-renewal, and squames are constantly shed from the skin surface at the final stage of differentiation.

Probiotics, collectively refers to microorganisms which have beneficial effects on the human body, and are microorganisms that offer benefit to our bodies. Most probiotics known to date are lactic acid bacteria. Probiotics have been reported to show efficacy through various beneficial effects on the human body, but there are few studies on a correlation between skin flora and skin.

The skin barrier consists of dead keratinocytes and intercellular lipids. The skin barrier is a skin protection layer that protects the skin against external stimuli and prevents evaporation of water through the skin, and plays a key role in maintaining skin health. That is, the skin barrier prevents excessive loss of water from the body and entry of harmful substances such as chemicals or microorganisms. Keratinocyte envelopes constituting the surface of dead keratinocytes play an important role in the stability of intercellular lipids. Keratinocytes undergo differentiation to form skin barriers through cornification. Functions of the skin barrier may be destroyed with aging or by external factors, and damage of the skin barrier may cause water loss of the skin and wrinkles.

Accordingly, the present inventors examined what changes occur in the skin according to changes of skin flora, and moreover, they studied whether the skin environment may be potentially improved by inducing changes of skin flora. As a result, a novel microorganism of the family Sporichthyaceae was isolated and identified from the skin of a healthy adult, and it was found that the novel microorganism or a culture thereof may induce changes in a skin microbial community so as to improve the skin environment, and may be used in skin-related conditions, thereby completing the present invention.

DETAILED DESCRIPTION OF THE INVENTION

Technical Problem

An aspect provides a novel microorganism of the genus *Epidermidibacterium* belonging to the family Sporichthyaceae.

Another aspect provides a culture of the microorganism.

Still another aspect provides a composition including the microorganism of the genus *Epidermidibacterium* or the culture thereof.

Still another aspect provides a composition for preventing, improving, or treating a condition of a subject, which include the microorganism of the genus *Epidermidibacterium* or the culture thereof.

Still another aspect provides use of the microorganism of the genus *Epidermidibacterium* or the culture thereof in preparation of the composition.

Still another aspect provides use of the microorganism of the genus *Epidermidibacterium* or the culture thereof in preparation of the composition for preventing, improving, or treating a condition of a subject.

Still another aspect provides a method of preventing, improving, or treating a condition of a subject, the method including administering the microorganism of the genus *Epidermidibacterium* or the culture thereof to a subject in need thereof.

Technical Solution

An aspect provides a novel microorganism of the genus *Epidermidibacterium* belonging to the family Sporichthyaceae.

The microorganism of the genus *Epidermidibacterium* may have one or more of the following mycological characteristics:
(1) rod-shaped;
(2) non-motile;
(3) Gram-positive;
(4) non-spore-forming;

(5) oxidase- and/or catalase-negative;

(6) MK-9(H4) is detectable therefrom;

(7) a polar lipid is one or more selected from the group consisting of phosphatidylethanolamine (PE), phosphatidylinositol (PI), phosphatidylglycerol (PG), phosphatidylcholine (PC), and three unidentified lipids (UL); and (8) a DNA G+C content is 68.9 mol %.

There are obvious distinctions in phylogenetic and chemotaxonomic characteristics between the microorganism of the genus *Epidermidibacterium* and other strains of different genera, and thus the microorganism was identified as a novel microorganism of the genus *Epidermidibacterium*.

The microorganism of the genus *Epidermidibacterium* may include *Epidermidibacterium keratini*.

The *Epidermidibacterium keratini* may have any one or more of the following mycological characteristics:

(1) 0.5 μm to 0.3 μm in length, and 0.3 μm to 0.1 μm in diameter;

(2) colonies are round, convex, and pale yellow;

(3) growth is observed on Reasoner's 2A (R2A) agar, but not on nutrient agar (NA), yeast extract malt extract agar (ISP 2), and trypticase soy agar (TSA);

(4) growth is observed on R2A agar at 15° C. to 35° C. (optimum temperature: 25° C.), but not at 10° C. or 40° C.;

(5) growth is observed at pH 5.0 to 6.5 and at a NaCl concentration of up to 10% (optimum pH 6.0, 0% NaCl);

(6) nitrate is reduced to nitrite;

(7) casein and starch are degraded, but DNA and carboxymethylcellulose are not degraded;

(8) characteristics described in Tables 1 to 3 are observed;

(9) positive for assimilation of one or more selected from the group consisting of N-acetyl-D-glucosamine, N-acetyl-β-D-mannosamine, α-D-glucose, D-mannose, D-fructose, D-galactose, dextrin, D-fucose, inosine, lactamide, maltotriose, D-psicose, D-ribose, α-ketovaleric acid, D-fructose-6-PO$_4$, L-serine, pectin, pyruvic acid, adenosine, thymidine, 2'-deoxy adenosine, adenosine-5'-monophosphate, p-hydroxy-phenylacetic acid, methyl pyruvate, D-lactic acid methyl ester, L-lactic acid, citric acid, α-keto-glutaric acid, D-malic acid, L-malic acid, bromo-succinic acid, tween 40, tween 80, α-hydroxy-butyric acid, β-hydroxy-D,L-butyric acid, α-keto-butyric acid, propionic acid, and acetic acid activities;

(10) negative for assimilation of one or more selected from the group consisting of D-maltose, D-cellobiose, gentiobiose, sucrose, D-turanose, stachyose, D-raffinose, α-D-lactose, D-melibiose, β-methyl-D-glucoside, D-salicin, N-acetyl-D-galactosamine, N-acetyl neuraminic acid, D-sorbitol, D-mannitol, D-arabitol, myo-inositol, glycerol, D-glucose-6-PO$_4$, D-aspartic acid, D-serine, gelatin, glycyl-L-proline, L-alanine, L-arginine, L-aspartic acid, L-glutamic acid, L-histidine, L-pyroglutamic acid, D-galacturonic acid, L-galactonic acid lactone, D-gluconic acid, D-glucuronic acid, glucuronamide, mucic acid, quinic acid, D-saccharic acid, α-amino-butyric acid, formic acid, α-cyclodextrin, β-cyclodextrin, glycogen, inulin, mannan, N-acetyl-D-glucosamine, N-acetyl-β-D-mannosamine, amygdalin, L-arabinose, arbutin, L-fucose, D-galactose, D-galacturonic acid, D-gluconic acid, lactulose, D-melezitose, α-methyl-D-galactoside, β-methyl-D-galactoside, 3-methyl glucose, α-methyl-D-glucoside, β-methyl-D-glucoside, α-methyl-D-mannoside, palatinose, L-rhamnose, salicin, sedoheptulosan, D-tagatose, D-trehalose, turanose, xylitol, D-xylose, acetic acid, α-hydroxybutyric acid, β-hydroxy-phenylacetic acid, D-lactic acid methyl ester, D-malic acid, L-malic acid, pyruvatic acid methyl ester, succinic acid mono-methyl ester, propionic acid, succinamic acid, N-acetyl-L-glutamic acid, L-alaninamine, D-alanine, L-alanyl-glycerin, glycyl-L-glutamic acid, L-pyroglutamic acid, putrescine, 2,3-butanediol, uridine, thymidine-5'-monophosphate, uridine-5'-monophosphate, D-fructose-6-phosphate, α-D-glucose-1-phosphate, D-glucose-6-phosphate, and D-L-α-glycerol phosphate;

(11) one or more activities selected from the group consisting of esterase (C4), esterase lipase (C8), leucine arylamidase, crystine arylamidase, acid phosphatase, and naphthol-AS-BI-phosphohydrolase activities are present;

(12) weak alkaline phosphatase, valine arylamidase, or α-chymotrypsin activity is present;

(13) one or more activities selected from the group consisting of lipase (C14), trypsin, α-galactosidase, β-glucuronidase, β-glucosidase, α-glucosidase, N-acetyl-β-glucosaminidase, α-mannosidase, and α-fucosidase activities are absent;

and

(14) major fatty acids are $C_{17:1}\omega 8C$, $C_{16:0}$, iso-$C_{15:0}$, or summed feature 3 ($C_{16:1}\ \omega 6c$ and/or $C_{16:1}\ \omega 7c$).

The microorganism of the genus *Epidermidibacterium* or *Epidermidibacterium keratini* may have any one or more of the following morphological characteristics:

(1) rod-shaped;

(2) non-motile;

(3) no flagella;

(4) Gram-positive;

(5) non-spore-forming;

(6) 0.5 μm to 0.3 μm in length, and 0.3 μm to 0.1 μm in diameter; and (7) colonies are round, convex, and pale yellow.

The microorganism of the genus *Epidermidibacterium* or *Epidermidibacterium keratini* may have any one or more of the following cultural and physiological characteristics:

(1) aerobic;

(2) heterotrophic;

(3) oxidase- and/or catalase-negative (4) characteristics of Table 1;

(5) growth is observed on R2A agar, but not on NA, ISP 2, and TSA;

(6) growth is observed on R2A agar at 15° C. to 35° C. (optimum temperature: 25° C.), but not at 10° C. or 40° C.;

(7) growth is observed at pH 5.0 to 6.5 and at a NaCl concentration of up to 10% (optimum pH 6.0, 0% NaCl);

(8) nitrate is reduced to nitrite; and (9) casein and starch are degraded, but DNA and carboxymethylcellulose are not degraded.

The microorganism of the genus *Epidermidibacterium* or *Epidermidibacterium keratini* may have any one or more of the following biochemical characteristics:

(1) tetrahydrogenated menaquinone with nine units (MK-9(H4)) is the only isoprenoid quinone detected;

(2) major polar lipids are any one or more selected from the group consisting of PE, PI, three UPL, PG, PC, two unidentified aminolipids (AL), and three UL;

(3) a DNA G+C content is 68.9 mol %; and (4) a fatty acid composition of Table 2.

The *Epidermidibacterium keratini* may include a 16s rRNA gene having a nucleotide sequence of SEQ ID NO: 1.

The *Epidermidibacterium keratini* may be deposited under Accession NO. KCCM 11843P.

Further, another aspect provides a culture of the microorganism of the genus *Epidermidibacterium* or *Epidermidibacterium keratini*.

As used herein, the term "culture" refers to a culture obtained by culturing the microorganism, a concentrate thereof, or a freeze-dried product thereof, or a culture supernatant obtained by removing the microorganism from the culture, a concentrate thereof, or a freeze-dried product thereof, and "culture supernatant", "conditioned culture", and "conditioned medium" may be used interchangeably therewith.

The culture may be obtained by culturing the microorganism of the genus *Epidermidibacterium* or *Epidermidibacterium keratini* in R2A medium at any temperature of higher than 10° C. or lower than 40° C. for a predetermined time, for example, 4 hours to 50 hours.

In a specific embodiment, the culture supernatant of the microorganism may be obtained by removing the microorganism from the culture of the microorganism by centrifugation or filtration.

In another specific embodiment, a concentrate may be obtained by concentrating the culture itself or a supernatant which is obtained by centrifuging the culture or filtering the culture by using a filter.

A medium and culture conditions for culturing the microorganism of the genus *Epidermidibacterium* may be appropriately selected or modified by those skilled in the art.

Still another aspect provides use of the microorganism of the genus *Epidermidibacterium* or the culture thereof in preparation of a composition, and particularly, provides a composition including the microorganism of the genus *Epidermidibacterium* or the culture thereof.

The microorganism of the genus *Epidermidibacterium* and the culture thereof are the same as described above.

In a specific embodiment, the microorganism of the genus *Epidermidibacterium* or the culture thereof may increase expression of filaggrin, claudin, αSMase, CerS3, transglutaminase-1, and HAS, and decrease expression of inflammation-related factors and pruritus-related factors. Therefore, the microorganism of the genus *Epidermidibacterium* may be usefully applied to skin-related conditions or inflammation-related conditions.

Examples of the skin-related conditions may include skin aging, wounds, dermatitis, atopic dermatitis, pruritus, eczematous dermatosis, dry eczema, erythema, urticaria, psoriasis, drug rash, papulosquamous disease, insect and parasite-mediated diseases, superficial dermatomycosis, bacterial infectious diseases, viral diseases, sexually transmitted diseases, autoimmune bullous diseases, connective tissue disease, dyschromatosis, xeroderma pigmentosum, acne, etc.

Examples of the inflammation-related conditions may include dermatitis, allergy, atopy, conjunctivitis, periodontitis, rhinitis, otitis media, sore throat, tonsillitis, pneumonia, gastric ulcer, gastritis, Crohn's disease, colitis, gout, ankylosing spondylitis, rheumatic fever, lupus, fibromyalgia, psoriatic arthritis, osteoarthritis, rheumatoid arthritis, shoulder arthritis, tendinitis, tenosynovitis, peritendinitis, myositis, hepatitis, cystitis, nephritis, sjögren's syndrome, multiple sclerosis, and acute and chronic inflammatory diseases.

The composition may include 0.001% by weight to 80% by weight, for example, 0.01% by weight to 60% by weight, 0.01% by weight to 40% by weight, 0.01% by weight to 30% by weight, 0.01% by weight to 20% by weight, 0.01% by weight to 10% by weight, 0.01% by weight to 5% by weight, 0.05% by weight to 60% by weight, 0.05% by weight to 40% by weight, 0.05% by weight to 30% by weight, 0.05% by weight to 20% by weight, 0.05% by weight to 10% by weight, 0.05% by weight to 5% by weight, 0.1% by weight to 60% by weight, 0.1% by weight to 40% by weight, 0.1 by weight to 30% by weight, 0.1% by weight to 20% by weight, 0.1% by weight to 10% by weight, or 0.1% by weight to 5% by weight of the microorganism or the culture thereof with respect to the total weight of the composition.

Hereinafter, use of the microorganism of the genus *Epidermidibacterium* according to compositions will be described in detail.

The composition may be a cosmetic composition.

In a specific embodiment, the cosmetic composition may enhance a skin barrier; prevent, improve, or inhibit aging; prevent or improve pruritus; and prevent or improve inflammation.

As used herein, the term "skin aging" refers to both tangible and intangible changes that appear on the skin with aging, and for example, decreased epidermal thickness, reduction in the number of dermal cells or blood vessels, reduced ability to repair DNA, decreased cell turnover, delayed wound healing, reduced skin barrier functions, reduced water retention in the epidermis, decreased sweat and sebum secretion, decreased vitamin D production, decreased physical damage defense, decreased chemical removal ability, decreased immune responsiveness, decreased sensory function, decreased temperature control, etc. The microorganism of the genus *Epidermidibacterium* or the culture thereof may be used to improve skin aging caused by exogenous or endogenous factors. The exogenous factors refer to many external factors, for example, ultraviolet rays (light), and the endogenous factors, also called chronological factors, refer to factors mainly occurring over time. That is, the skin aging specifically includes not only early aging caused by external stimuli such as UV, air pollution, cigarette smoke, chemicals, etc., but also natural aging occurring due to a reduction in skin cell proliferation with aging. The skin aging is a concept including all of wrinkles, loss of elasticity, saggy skin, dryness, etc. Further, wrinkles include wrinkles caused by changes in the components constituting the skin tissue by stimulation of internal/external factors.

Therefore, since the composition may have the above effects, it may be used for skin improvement, for example, skin moisturizing, skin aging prevention, skin barrier reinforcement, skin wound healing, or skin inflammation inhibition.

The cosmetic composition may have, for example, a cosmetic formulation of a softening toner, a nutrient toner, a massage cream, a nutritional cream, an essence, a pack, a gel, an ampoule, or a type of skin adhesive.

The cosmetic composition may include components commonly used in cosmetic compositions, for example, common additives and carriers such as a stabilizer, a solubilizer, vitamins, a pigment, and a fragrance, in addition to the composition as an active ingredient.

Further, the composition may be a composition for external use.

In the present disclosure, the composition for external use may be a cream, a gel, an ointment, a skin emulsifier, a skin suspension, a transdermal patch, a drug-containing bandage, a lotion, or a combination thereof. The composition for external use may be appropriately blended with components used in compositions for external use, such as common cosmetics or medicines, for example, an aqueous component, an oily component, a powder component, alcohols, a moisturizer, a thickener, a UV absorber, a whitening agent, a preservative, an antioxidant, a surfactant, a fragrance, a pigment, a variety of skin nutrients, or a combination thereof as needed. The composition for external use may be appropriately blended with a sequestering agent such as disodium edetate, trisodium edetate, sodium citrate, sodium polyphosphate, sodium metaphosphate, gluconic acid, etc., caffeine, tannine, verapamil, a licorice extract, glabridin, a hot water extract of fruits of Calin, various herbal medicines, tocopheryl acetate, glycyrrhizic acid, tranexamic acid and a derivative or salt thereof, vitamin C, magnesium ascorbyl phosphate, ascorbic acid glucoside, arbutin, Kojic acid, sugars such as glucose, fructose, treharose, etc.

In another specific embodiment, the composition may be a pharmaceutical composition.

The pharmaceutical composition may further include a pharmaceutically acceptable diluent or carrier. The diluent may be lactose, corn starch, soybean oil, microcrystalline cellulose, or mannitol, and a lubricant may be magnesium stearate, talc, or a combination thereof. The carrier may be an excipient, a disintegrating agent, a binder, a lubricant, or a combination thereof. The excipient may be microcrystalline cellulose, lactose, low-substituted hydroxy cellulose, or a combination thereof. The disintegrating agent may be calcium carboxymethylcellulose, sodium starch glycolate, anhydrous dibasic calcium phosphate, or a combination thereof. The binder may be polyvinylpyrrolidone, low-substituted hydroxypropyl cellulose, hydroxypropyl cellulose, or a combination thereof. The lubricant may be magnesium stearate, silicon dioxide, talc, or a combination thereof.

The pharmaceutical composition may be formulated as a preparation for oral or parenteral administration. The preparation for oral administration may be granules, a powder, a liquid, a tablet, a capsule, a dry syrup, or a combination thereof. The preparation for parenteral administration may be an injectable formulation.

The composition may be a health functional food composition.

In the health functional food composition, the microorganism of the genus *Epidermidibacterium* or the culture thereof may be used alone or in combination with other foods or food ingredients, according to a general method. A mixing ratio of the active ingredient may be determined according to the purpose of use (prevention, health, or treatment). In general, to produce foods or beverages, the composition of the present disclosure may be added in an amount of 15 parts by weight or less with respect to a raw material. There is no particular limitation in kinds of the health functional food. Of the kinds of the health functional food, a beverage composition may include various flavors or natural carbohydrates as an additional ingredient, like common beverages. The natural carbohydrates include monosaccharides such as glucose and fructose, disaccharides such as maltose and sucrose, polysaccharides such as dextrin and cyclodextrin, and sugar alcohols such as xylitol, sorbitol, and erythritol. As a sweetener, natural sweeteners such as thaumatin and stevia extract, or synthetic sweeteners such as saccharin and aspartame may be used. The health food composition may include nutrients, vitamins, minerals, flavors, coloring agents, pectic acid and salts thereof, alginic acid and salts thereof, organic acids, protective colloidal thickeners, pH regulators, stabilizers, preservatives, glycerins, alcohols, sparkling components for carbonated beverages, or a combination thereof. The health functional food composition may also include natural fruit juice, fruit juice beverages, fruit flesh for the preparation of vegetable beverages, or a combination thereof.

Further, still another aspect provides a method of preventing, improving, or treating a condition of a subject, the method including treating or administering an effective amount of the microorganism of the genus *Epidermidibacterium*, the culture thereof, or the composition including the same to a subject in need thereof.

The condition of a subject may be a skin-related condition or an inflammation-related condition.

The composition is the same as described above. The subject may be mammals, for example, humans, cattle, horses, pigs, dogs, sheep, goats, or cats.

Advantageous Effects of the Invention

The novel microorganism of the family Sporichthyaceae, according to an aspect, has phylogenetic and chemotaxonomic characteristics distinct from those of other microorganisms of different genera of the same or different family, and thus the microorganism of the family Sporichthyaceae or a culture thereof may be effectively used for preventing, improving, or treating skin-related conditions or inflammation-related conditions.

DESCRIPTION OF THE DRAWINGS

FIG. 4 is a diagram showing changes in skin flora according to EPI-7 treatment;

BEST MODE

Hereinafter, the present disclosure will be described in more detail with reference to Examples. However, these Examples are for illustrative purposes only, and the scope of the present disclosure is not intended to be limited by these Examples.

Example 1. Isolation of Microorganism

A sample (human epidermal keratinocyte) obtained by washing the skin of a healthy woman with sterile distilled water was seeded in a Reasoner's 2A (R2A) medium (Becton Dickinson, Cockeysville, Md.). After seeding, the sample was incubated for 48 hours in an incubator at 28° C., and 100 colonies were isolated and cultured, followed by re-incubation for 48 hours in an incubator at 28° C. The completely cultured colonies were identified by 16s rRNA gene sequencing. Primers (SEQ ID NOS: 2 and 3) used at this time were designed to react and amplify only in bacteria. PCR amplification was performed for 30 cycles of at 95° C. for 1 min, at 55° C. for 1 min, and at 75° C. for 1 min and 30 sec, and lastly, at 72° C. for 8 min. A product was stored at 4° C. DNA sequences of species isolated and cultured after PCR reaction were determined by using an ABI-3730XL (ABI, USA). Nucleotide sequences of 16S rRNA regions determined in the isolated and cultured colonies of the microorganisms were compared with those of other strains registered in the BLAST program provided through the National Center for Biotechnology Information (NCBI)'s homepage. Only novel species with homology of 97% or less were selected and used, and of them, a novel microorganism with homology of 94% or less (hereinafter, referred to as "EPI-7") was selected. EPI-7 has a 16s rRNA sequence of SEQ ID NO: 1 (complementary DNA).

Example 2. Phylogenetic and Mycological Characteristics of Novel Microorganism 2.1. Phylogenetic Characteristics 16S rRNA homology analysis was calculated using an ExTaxon-e server (Yoon S. H et al., (2017)). Sequence data were aligned using a software package BioEdit (Hall T. A. (1999)), and phylogenetic analysis was performed using MEGA version 5.05 (Tamura, K et al. (2011)). Phylogenetic trees were constructed using Neighbor-joining (Sitouand Nei (1987)), maximum-likelihood, and maximum-parsimony algorithms, and stability of the phylogenetic trees was evaluated by bootstrap analysis (1000 replications) (Felsenstein 1985).

Figure 1:
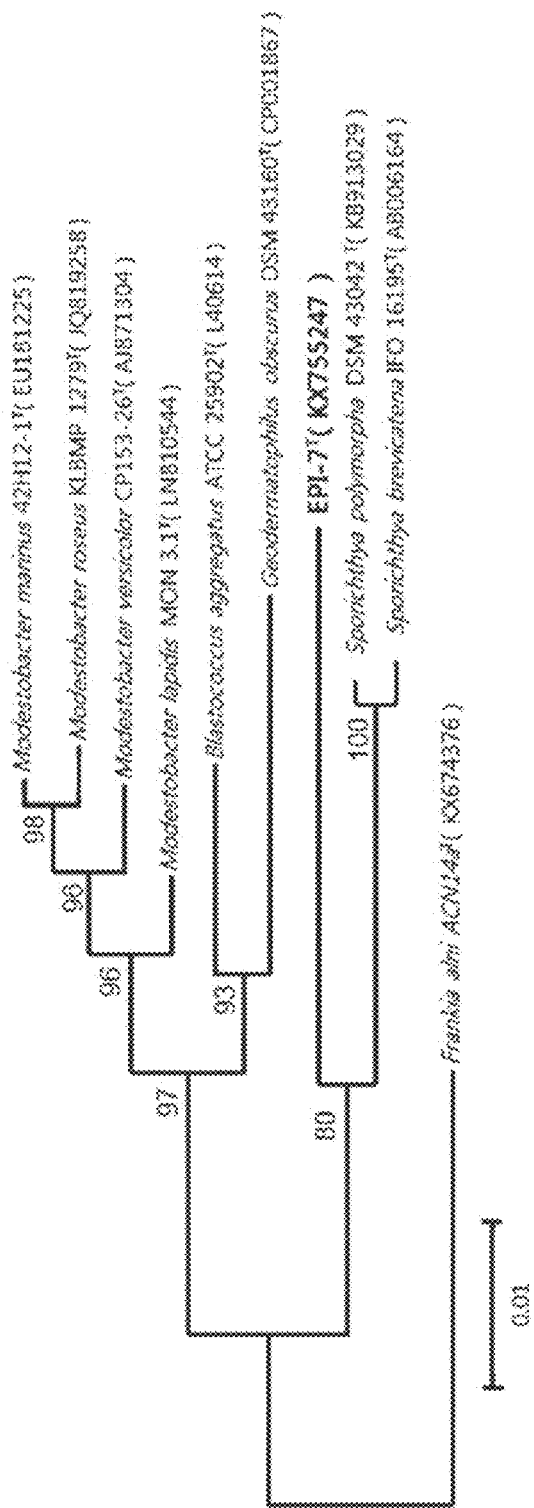
FIG. 1 is a diagram showing a phylogenetic result for EPI-7.

As a result, EPI-7 was found to have 93.4%, 93.2%, 93.0%, 93.0%, and 92.9% homology with *Modestobacter lapidis* MON 3.1, *Sporichthya polymorpha* DSM 43042, *Modestobacter marinus* 42H12-1, *Modestobacter roseus* KLBMP1279, and *Modestobacter versicolor* CP153-2, respectively. As shown in FIG. 1, results of a constructed phylogenetic tree showed that EPI-7 is a novel microorganism belonging to the family Sporichthyaceae, which has not yet been reported.

2.2. Mycological Characteristics 2.2.1. Morphological Characteristics

Morphological characteristics of EPI-7 were analyzed as follows.

First, cell morphology of EPI-7 was observed under an Olympus microscope (GX71) at magnification of 1000× after culturing cells in R2A medium at 25° C. for 5 days. Gliding motility was investigated by subjecting a hanging-drop technique to fresh EPI-7 cells in R2A medium.

For scanning electron microscopy (SEM), a sample was pretreated as follows. EPI-7 was seeded on R2A (Becton Dickinson, Cockeysville, Md.) solid medium and incubated for 3 days, and then a membrane filter was attached to formed colonies.

The membrane filter having colonies attached thereto was separated and fixed in a 2.5% glutaraldehyde solution for 2 hours, and then washed with PBS for 5 minutes twice.

Figure 2:
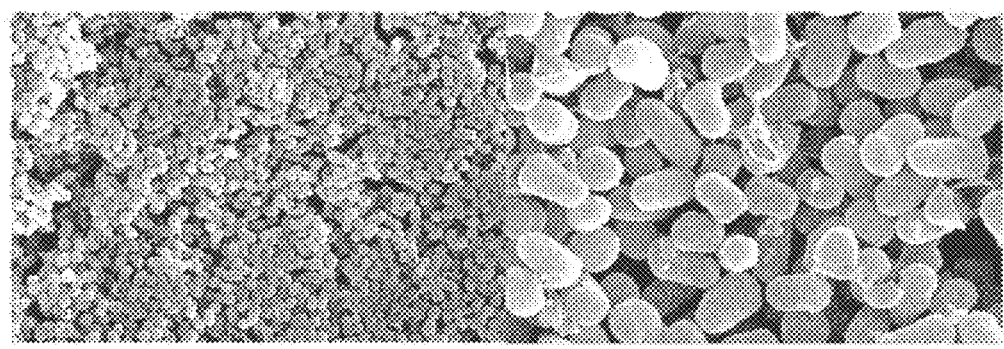
FIG. 2 is a diagram showing morphological characteristics of EPI-7.

Thereafter, the membrane filter was treated with a 2% osmium tetroxide solution for 1 hour, and dehydrated with 40%, 50%, 60%, 70%, 80%, 90%, and 100% ethanol. The dehydrated sample was treated with isoamylacetate to remove ethanol therefrom. The pre-treated sample was naturally dried, and sputtered with gold by using a sputter coater (SC502, Polaron). Thereafter, the sample was photographed using SEM (Hitachi S4300N, Hitachi, Japan) at magnification of 1000× and 100000×, and results are shown in FIG. 2.

To distinguish between gram-positive and gram-negative bacteria, experiments were performed as follows.

In detail, one colony of EPI-7 cultured well on the R2A solid medium was collected and fixed on a slide glass. The slide glass was completely dried, and then stained with crystal violet for 1 to 2 minutes, and washed with running water and dried again.

The dried slide was stained with iodine-potassium iodide for 1 minute. Thereafter, the slide was destained with ethyl alcohol, and washed with running water, followed by drying. To determine whether the sample was Gram-positive or -negative, secondary staining was performed using a red staining dye such as Safranin for 1 to 3 minutes, and the slide was washed with water and observed under a microscope (Olympus microscope, 12 GX71).

As a result, EPI-7 was found to have the following morphological characteristics:

(1) rod-shaped;
(2) non-motile;
(3) no flagella;
(4) Gram-positive;
(5) non-spore-forming;
(6) 0.5 µm to 0.3 µm in length, and 0.3 µm to 0.1 µm in diameter; and
(7) colonies are round, convex, and pale yellow.

2.2.2. Cultural and Physiological Characteristics

To investigate culture conditions of EPI-7, an optimum culture temperature was determined by setting an optimum growth temperature from 5° C. to 40° C. (5° C. intervals), and an optimum salt concentration was determined by adding NaCl of 0% (w/v) to 15% (w/v) (0.5% interval) to a medium and then culturing at 25° C. for 5 days.

pH was determined by using the following buffer system; sodium acetate/acetic acid (pH<6), Tris/HCl (pH 6 to pH 9), and glycine/sodium hydroxide (pH>9).

Further, catalase activity was determined by analyzing bubble generation in 3% (v/v) $H_2O_2$, and oxidase activity was determined by using 1% (w/v) tetramethyl phenylenediamine.

Further, in order to test growth media, nutrient agar (NA), yeast extract malt extract agar (ISP 2), and trypticase soy agar medium (BD, USA) were used for culturing at 25° C. for 5 days.

Further, BioLog GP2, BioLog Gen III, API 20NE, and API ZYM (biomeriuex, France) were used to investigate substance utilization of EPI-7. A method of use was performed according to the manual provided by the manufacturer. When a positive reaction occurs, a violet color develops. After examination with the naked eye, the degree of growth was accurately determined using a microplate spectrophotometer. An API ZYM test was analyzed after incubation at 25° C. for 4 hours, and another API test was analyzed after incubation at 25° C. for at least 48 hours. Results of a comparison with other species are shown in the following Table 1.

Anaerobic growth was examined in serum bottles by adding sodium thioglycollate (1 g/l) to R2A medium, and replacing the upper air layer with nitrogen gas.

Tests for degradability of DNA, casein, starch, tween 80, and carboxymethyl cellulose were performed after incubation at 25° C. for 7 days.

TABLE 1

| Characteristic | 1 | 2 | 3 | 4 |
|---|---|---|---|---|
| API-ZYM test | | | | |
| Esterase(C4) | + | + | + | − |
| Esterase lipase(C8) | + | − | + | − |
| Lipase(C14) | − | − | + | − |
| Valine arylamidase | − | + | + | + |
| Acid phosphatase | + | + | − | + |
| α-Glucosidase | − | + | − | + |
| β-glucosidase | − | + | − | + |
| BIOLOG GP2/GENIII tests Assimilation of | | | | |
| Dextrin | + | + | − | − |
| Tween 40 | + | + | + | + |
| Tween 80 | + | + | − | − |
| D-Fructose | + | − | − | + |
| Maltotriose | + | − | − | − |
| α-D-Glucose | − | + | + | + |
| 3-Methyl Glucose | − | − | + | − |
| D-Glucose-6-PO$_4$ | − | + | + | − |
| D-Galactose | − | − | − | + |
| D-Fructose-6-PO$_4$ | − | + | + | − |
| D-Glucuronic Acid | − | − | − | + |
| D-Mannose | + | − | − | − |
| D-Psicose | + | + | − | − |
| D-Ribose | + | + | − | − |
| D-Sorbitol | − | + | − | + |
| L-Histidine | − | − | + | − |
| Pectine | − | + | + | + |
| Citric acid | − | + | + | + |
| L-Malic Acid | − | + | + | + |
| α-Hydroxybutyric Acid | + | − | − | + |
| α-Ketoglutaric Acid | + | + | − | − |
| β-Hydroxy-D,L-Butyric Acid | − | − | + | − |
| Acetoacetic Acid | − | + | + | + |
| Acetic acid | − | + | − | + |
| D-Fructose-6-PO$_4$ | − | + | + | − |
| D-Galacturonic Acid | − | + | + | − |
| Glucuronamide | − | + | + | − |
| L-Lactic Acid | − | − | − | + |
| L-Serine | + | − | − | − |
| Growth in presence of inhibitory compounds | | | | |
| Aztreonam | − | − | + | + |
| Guanidine HCl | − | − | − | − |
| Lithium chloride | + | + | − | + |
| Niaproof 4 | − | − | − | − |
| Tetrazolium blue | + | + | − | − |
| Tetrazolium violet | + | + | − | + |
| Troleandomycin | + | + | − | − |
| Vancomycin | + | + | − | − |
| Nalidixic Acid | + | + | + | + |
| Rifamycin SV | − | + | + | |

TABLE 1-continued

| Characteristic | 1 | 2 | 3 | 4 |
|---|---|---|---|---|
| Potassium Tellurite | − | + | + | + |
| Growth at pH 5.0 | + | − | − | − |
| Growth in the presence of 10% (w/v) NaCl | + | − | − | − |

1: EPI-7
2: *Modestobacter lapidis* MON 3.1
3: *Sporichthya polymorpha* DSM 43042
4: *Modestobacter marinus* 42H12-1
+: positive
−: negative As a result, EPI-7 was found to have the following cultural and physiological characteristics:
(1) aerobic;
(2) heterotrophic;
(3) oxidase- and/or catalase-negative
(4) characteristics of Table 1;
(5) growth is observed on R2A agar, but not on NA, ISP 2, and TSA;
(6) growth is observed on R2A agar at 15° C. to 35° C. (optimum temperature: 25° C.), but not at 10° C. or 40° C.;
(7) growth is observed at pH 5.0 to 6.5 and at a NaCl concentration of up to 10% (optimum pH 6.0, 0% NaCl);
(8) nitrate is reduced to nitrite; and
(9) casein and starch are degraded, but DNA and carboxymethylcellulose are not degraded.

2.2.3. Biochemical Characteristics

A DNA G+C content of EPI-7 was analyzed by HPLC. In detail, experimental methods and conditions for analyzing a cellular fatty acid composition, a G+C composition, and quinone are as follows.

First, the cellular fatty acid composition of the isolated microorganism was analyzed according to Miller's method. About 40 mg of cultured cells were transferred to a tube, and 1 ml of a solution prepared by adding 15% NaOH to 50% methanol was added thereto, and the tube was heated to 100° C. for 30 minutes and cooled at room temperature. 2 ml of methanolic-HCl (a mixture of 325 ml of 6.0 N HCl and 275 ml of methanol) was added to the tube, which was then heated at 80° C. for 10 minutes, and then rapidly cooled. 1.25 ml of hexane/methyl-tert-butylether (1:1, v/v) was added thereto, and mixed well for 10 minutes. After being left at room temperature, when the reaction solution was separated into 2 layers, a lower layer was removed, and 3 ml of dilute NaOH (10.8 g of NaOH/900 ml of D.W) was added and mixed well for 10 minutes and left at room temperature. About ⅔ of a supernatant was transferred to a screw-capped sample vial (12×32 mm, Agilent technologies), and capped, and then used as a sample. The sample was subjected to saponification, methylation, and extraction according to a standard protocol of Sherlock MIS Software. Fatty acids were analyzed by using an Agilent Technologies 6890 Gas Chromatograph, an A30 m×0.320 mm×0.25 μm methyl siloxane column (HP-1), and the TSBA40 database (MIDI, Version 4.5) of the MIS package was used to identify the fatty acids.

All experiments were repeated at least three times, and the results are shown in the following Table 2.

Further, G+C mol % was analyzed as follows. A DNA solution extracted from the microorganism was transferred to a microtube, and centrifuged at 14000 rpm for 5 minutes. Thereafter, 100 μl of a supernatant was collected and transferred to a new tube, and DNA denaturation was performed at 100° C. for 5 minutes, and then cooled. 10 μl (0.1 mg/mL) of P1 nuclease was added thereto, and allowed to react at 50° C. for 3 hours. Alkaline phosphatase (10 μl of buffer, and 5 μl of phosphatase) was added thereto, followed by incubation at 37° C. overnight. After centrifugation at 14000 rpm for 5 minutes, analysis was performed under the following conditions:

HPLC: YOUNG LIN YL9100 (YL9111 Binary pump)
    Detector: YOUNG LIN YL9120 UV/Vis Detector
    Chromatograph data system: YOUNG LIN Autochro-3000
    Analysis column: Waters Spherisorb 5 um ODS 2 4.6 mm×250 mm column
    Eluent: 0.02M $NH_4H_2PO_4$ (pH non-adjusted)-acetonitrile (20:1, v/v)
    Flow rate: 0.5 mL/min
    Detection wavelength: 270 nm Quinone was analyzed as follows: The microorganism was cultured at 25° C. for 96 hours in R2A medium and then only cells were collected therefrom and freeze-dried. The freeze-dried sample was extracted under the following conditions: Chloroform:methanol (2:1) solution was added and shaken for 3 to 4 hours. Cells were filtered out using a filter paper (whatman No. 2) and a filtrate was concentrated. Thereafter, the concentrate was dissolved in 100 μl of Chloroform:methanol (8.5:1.5), and then centrifuged at 14000 rpm for 5 minutes to collect a supernatant, which was analyzed by HPLC. HPLC conditions were as follows:

HPLC: YOUNG LIN YL9100 (YL9111 Binary pump)
    Detector: YOUNG LIN YL9120 UV/Vis Detector
    Chromatograph data system: YOUNG LIN Autochro-3000
    Analysis column: Waters Spherisorb 5 um ODS 2 4.6 mm×150 mm column (column temp. 40° C.)
    Analysis solvent: methanol:isopropyl ether (4:1)
    Flow rate: 1.0 mL/min
    Detection wavelength: 254 mm.

Polar lipid analysis was performed after culturing the microorganism at 25° C. for 96 hours in R2A medium. First, polar lipids were extracted from the microorganism according to a method described in Minnikin D. E. et al. (1984)(J Microbiol Methods 2, 233-241). Thereafter, polar lipids were identified by two-dimensional TLC (Komakata K et al., 1987, Methods Microbiol 19, 161-206).

TABLE 2

| Fatty Acids(%) | 1 | 2 | 3 | 4 |
| --- | --- | --- | --- | --- |
| $C_{12:0}$ | 0.6 | — | 0.6 | — |
| Iso-$C_{13:0}$ | 0.1 | — | — | 0.1 |
| $C_{13:0}$ | 0.9 | — | 0.5 | — |
| Iso-$C_{14:0}$ | 1.9 | — | — | 2.4 |
| $C_{14:1}\,\omega 5c$ | 0.2 | — | — | — |
| $C_{14:0}$ | 1.6 | 6.8 | 1.7 | 0.5 |
| Iso-$C_{15:0}$ | 10.1 | 13.1 | — | 4.5 |
| Anteiso-$C_{15:0}$ | 3.2 | 1.6 | — | 6.5 |
| $C_{15:1}\,\omega 8c$ | 2.6 | 0.5 | — | — |
| $C_{15:1}\,\omega 6C$ | 1.1 | — | — | 1.2 |
| $C_{14:0}$ 2OH | 0.2 | — | — | — |
| Iso-$C_{16:1}$ H | 1.0 | 0.4 | — | 9.2 |
| Iso-$C_{16:0}$ | 8.5 | 4.6 | 1.7 | 28.4 |
| $C_{16:1}\,\omega 9c$ | 3.2 | — | — | — |
| $C_{16:0}$ | 18.4 | 14.2 | 22.4 | 5.1 |
| $C_{15:0}$ 2OH | 0.5 | — | — | — |
| Iso-$C_{17:0}$ | 0.4 | 0.7 | — | 1.6 |
| Anteiso-$C_{17:0}$ | 2.1 | 0.8 | — | 6.1 |
| $C_{17:1}\,\omega 8c$ | 19.9 | 5.8 | 21.2 | 11.8 |
| $C_{17:0}$ | 7.1 | 4.4 | 11.8 | 4.9 |
| 10-methyl $C_{17:0}$ | — | — | 8.9 | — |
| $C_{16:0}$ 2OH | 0.6 | 0.5 | — | — |
| $C_{18:3}\,\omega 6c(6,9,12)$ | 0.6 | 1.4 | 0.5 | — |
| $C_{18:1}\,\omega 9c$ | 2.5 | 5.4 | 10.4 | 1.1 |
| $C_{18:0}\,\omega 5c$ | 0.1 | — | — | — |
| $C_{18:0}$ | 1.1 | 8.7 | 4.0 | 0.7 |
| 10-methyl $C_{18:0}$ | | | 4.7 | |
| 11-methyl $C_{18:1}\,\omega 7c$ | 0.1 | — | — | — |
| $C_{19:0}$ | — | 3.6 | — | — |
| $C_{20:0}$ | — | 6.9 | — | — |
| Summed Feature 3 | 10.0 | 13.27 | 9.2 | 5.4 |
| Summed Feature 4 | 0.2 | — | — | — |
| Summed Feature 7 | — | 1.6 | — | 0.2 |
| Summed Feature 8 | 1.2 | 1.9 | 0.7 | 1.4 |
| Summed Feature 9 | — | 0.1 | 1.8 | 0.9 |

1: EPI-7
2: *Modestobacter lapidis* MON 3.1
3: *Sporichthya polymorpha* DSM 43042
4: *Modestobacter marinus* 42H12-1
Summed Feature 3: $C_{16:1}\,\omega 6c$ and/or $C_{16:1}\,\omega 7c$
Summed Feature 4: antesio B-$C_{17:1}$ and/or Iso I-$C_{17:1}$
Summed Feature 7: $C_{19:1}\,\omega 6c$ and/or $\omega 7c$ and/or $CycloC_{19:0}$
Summed Feature 8: $C_{18:1}\,\omega 6c$
Summed Feature 9: Iso $C_{17:1}\,\omega 9c$ As a result, EPI-7 was found to have the following biochemical characteristics:

(1) tetrahydrogenated menaquinone with nine units (MK-9(H4)) is the only isoprenoid quinone detected;

(2) major polar lipids are PE, PI, three UPL, PG, PC, two unidentified aminolipids (AL), and three UL;

(3) a DNA G+C content is 68.9 mol %; and (4) a fatty acid composition as shown in Table 2.

Further, its characteristics were compared with those of other microorganisms, and summarized in the following Table 3.

TABLE 3

| | EPI-7 | S. polymorpha | S. brevicatena | M. lapidis | M. versicolor | M. roseus | M. marinus |
| --- | --- | --- | --- | --- | --- | --- | --- |
| Cell morphology | Whitish Yellow, Short rod | Greyish White, Short aerial hyphae | Greyish White, Short aerial hyphae | Dark Orange, short rods and cocci | Pink-Deep Orange, Short rod | Pink, Short rod or cocci | Resish Orange, Short rod |
| Pigment on R2A | − | − | − | − | + | − | + |
| Growth in 10% NaCl | + | − | − | − | W | + | − |
| Major cellular fatty acids | C17:1ω8c, C16:0, iso-C15:0 and C16:1ω6c and/or C16:1ω7c | C16:0 and C17:1 | Iso-C16:0 | iso-C15:0, iso-C16:0, C16:1, ω9c and C16:0 | iso-C15:0, iso-C16:0, anteiso-C15:0 and C18:1 | Iso-C16:0 and iso-C15:0 | iso-C16:0 and C1:1 ω 8c. |

TABLE 3-continued

| | EPI-7 | S. polymorpha | S. brevicatena | M. lapidis | M. versicolor | M. roseus | M. marinus |
|---|---|---|---|---|---|---|---|
| Cell wall diamino acids | meso-DAP | LL-DAP | LL-DAP | meso-DAP | meso-DAP | meso-DAP | meso-DAP |
| G + C mol % | 68.9 | 71.0 | 71.6 | 72.0 | 73.0 | 71.7 | 72.3 |
| Cell wall sugars | Galactose Arabinose | Inositol, Mannose, Glycerol, Glucose | Glucosamine, Mannose, Galactose, Glucose | Glucose, Galactose, Ribose, Arabinose | Galactose Ribose Glucose | Galactose Ribose Glucose | Galactose Ribose Glucose |
| Major quinone | MK-9 (H4) | MK-9 (H6) | MK-9 (H8) | MK-9 (H4) | MK-9 (H4) | MK-9 (H4) | MK-9 (H4) |

As shown in Table 3, EPI-7 is different from the closest species in terms of major biochemical characteristics, and these chemotaxonomic results and the phylogenetic results of Example 2.1. demonstrate that EPI-7 is a new species.

Taken together, it was demonstrated that EPI-7 isolated from human epidermal keratinocytes is a microorganism of a novel genus belonging to the family Sporichthyaceae, and designated as *Epidermidibacterium* gen.nov. according to the phylogenetic nomenclature; *Epidermidibacterium* [E.pi.der.mi.di.bac.te'ri.um. N.L. n. epidermis, -idis skin; L. neut. n. bacterium, (a small rod or staff); N.L. neut. (*Epidermidibacterium* a small rod from the skin)].

Further, as confirmed in Example 2, *Epidermidibacterium* gen.nov. has the following characteristics:
(1) rod-shaped;
(2) non-motile;
(3) Gram-positive;
(4) non-spore-forming;
(5) oxidase- and/or catalase-negative;
(7) MK-9(H4) is detectable therefrom;
(8) major polar lipids are PE, PI, PG, PC, and three UL; and
(9) a DNA G+C content of 68.9 mol %.

Subsequently, the above results demonstrated that the *Epidermidibacterium* gen.nov. strain isolated from human epidermal keratinocytes is one species, which was designated as *Epidermidibacterium keratini* sp. nov according to the phylogenetic nomenclature;

*Epidermidibacterium keratini* (ke.ra.ti'ni. N.L. gen. neut. n. *keratini* pertaining to keratin).

Further, as confirmed in Example 2, *Epidermidibacterium keratini* has the following characteristics in addition to the characteristics of the *Epidermidibacterium* gen.nov:
(1) 0.5 µm to 0.3 µm in length, and 0.3 µm to 0.1 µm in diameter;
(2) colonies are round, convex, and pale yellow;
(3) growth is observed on Reasoner's 2A (R2A) agar, but not on nutrient agar (NA), yeast extract malt extract agar (ISP 2), and trypticase soy agar (TSA);
(4) growth is observed on R2A agar at 15° C. to 35° C. (optimum temperature: 25° C.), but not at 10° C. or 40° C.;
(5) growth is observed at pH 5.0 to 6.5 and at a NaCl concentration of up to 10% (optimum pH 6.0, 0% NaCl);
(6) nitrate is reduced to nitrite;
(7) casein and starch are degraded, but DNA and carboxymethylcellulose are not degraded;
(8) characteristics described in Tables 1 to 3 are observed;
(9) positive for assimilation of N-acetyl-D-glucosamine, N-acetyl-β-D-mannosamine, α-D-glucose, D-mannose, D-fructose, D-galactose, dextrin, D-fucose, inosine, lactamide, maltotriose, D-psicose, D-ribose, α-ketovaleric acid, D-fructose-6-PO$_4$, L-serine, pectin, pyruvic acid, adenosine, thymidine, 2'-deoxy adenosine, adenosine-5'-monophosphate, β-hydroxy-phenylacetic acid, methyl pyruvate, D-lactic acid methyl ester, L-lactic acid, citric acid, α-ketoglutaric acid, D-malic acid, L-malic acid, bromo-succinic acid, tween 40, tween 80, α-hydroxy-butyric acid, β-hydroxy-D,L-butyric acid, α-keto-butyric acid, propionic acid, and acetic acid activities;

(10) negative for assimilation of D-maltose, D-cellobiose, gentiobiose, sucrose, D-turanose, stachyose, D-raffinose, α-D-lactose, D-melibiose, β-methyl-D-glucoside, D-salicin, N-acetyl-D-galactosamine, N-acetyl neuraminic acid, D-sorbitol, D-mannitol, D-arabitol, myo-inositol, glycerol, D-glucose-6-PO$_4$, D-aspartic acid, D-serine, gelatin, glycyl-L-proline, L-alanine, L-arginine, L-aspartic acid, L-glutamic acid, L-histidine, L-pyroglutamic acid, D-galacturonic acid, L-galactonic acid lactone, D-gluconic acid, D-glucuronic acid, glucuronamide, mucic acid, quinic acid, D-saccharic acid, γ-amino-butyric acid, formic acid, α-cyclodextrin, β-cyclodextrin, glycogen, inulin, mannan, N-acetyl-D-glucosamine, N-acetyl-β-D-mannosamine, amygdalin, L-arabinose, arbutin, L-fucose, D-galactose, D-galacturonic acid, D-gluconic acid, lactulose, D-melezitose, α-methyl-D-galactoside, β-methyl-D-galactoside, 3-methyl glucose, α-methyl-D-glucoside, β-methyl-D-glucoside, α-methyl-D-mannoside, palatinose, L-rhamnose, salicin, sedoheptulosan, D-tagatose, D-trehalose, turanose, xylitol, D-xylose, acetic acid, γ-hydroxybutyric acid, β-hydroxy-phenylacetic acid, D-lactic acid methyl ester, D-malic acid, L-malic acid, pyruvatic acid methyl ester, succinic acid mono-methyl ester, propionic acid, succinamic acid, N-acetyl-L-glutamic acid, L-alaninamine, D-alanine, L-alanyl-glycerin, glycyl-L-glutamic acid, L-pyroglutamic acid, putrescine, 2,3-butanediol, uridine, thymidine-5'-monophosphate, uridine-5'-monophosphate, D-fructose-6-phosphate, α-D-glucose-1-phosphate, D-glucose-6-phosphate, and D-L-α-glycerol phosphate;

(11) esterase (C4), esterase lipase (C8), leucine arylamidase, crystine arylamidase, acid phosphatase, and naphthol-AS-BI-phosphohydrolase activities are present;

(12) weak alkaline phosphatase, valine arylamidase, and α-chymotrypsin activities are present;

(13) lipase (C14), trypsin, α-galactosidase, β-glucuronidase, β-glucosidase, α-glucosidase, N-acetyl-β-glucosaminidase, α-mannosidase, and α-fucosidase activities are absent; and

(14) major fatty acids are $C_{17:1}\omega 8C$, $C_{16:0}$, iso-$C_{15:0}$, or summed feature 3 ($C_{16:1}\omega 6c$ and/or $C_{16:1}\omega 7c$).

The present inventors deposited the *Epidermidibacterium keratini* strain belonging to the genus *Epidermidibacterium* at the Korean Culture Center of Microorganisms (KCCM) in the Korea Research Institute of Bioscience and Biotechnology on Jun. 8, 2016 with Accession NO: KCCM 11843P.

Example 3. Activity of Microorganism 3.1. Analysis of Skin-Microbiome Change

In order to measure the effect of EPI-7 on changes of skin flora, changes of the skin microbiome of a subject was analyzed.

In detail, EPI-7 culture was applied to the skin of the subject at 6-hr intervals, and skin samples were collected for a total of 72 hours and analyzed. Samples were collected before treatment of the culture (Epidermis A) and at 72 hours after treatment of the culture (Epidermis B). The samples were collected using sterile water and a scraper, and all procedures were performed on a clean bench. The samples collected from the skin were suspended in 0.85% NaCl, and supernatants were centrifuged (17,000 rpm/m) to collect cells therefrom. The cells were washed once with sterile physiological saline. Thereafter, DNA was extracted using a FastDNA SPIN KIT (MP Biomedical, France). For amplification of 16S ribosomal DNA genes of the extracted DNA, GC clamp (SEQ ID NO: 4)-attached 341F (SEQ ID NO: 5) and 518R (SEQ ID NO: 6) were used. For a PCR reaction, 0.4 mM dNTP, 0.5 units of Taq polymerase, and 10 µl of 4 mM $Mg^{2+}$-containing Takara Perfect Premix (Takara, Japan) were mixed with 1 µl of a DNA template (20 µg/mL), and 1 µl each of 1.0 µM forward primer and 1.0 µM reverse primer. Sterile water was added to the mixture to a total volume of 20 µl. The PCR reaction was performed in a C1000-Dual (Bio-Rad, USA) by touchdown PCR in which temperature was decreased from 64° C. to 59° C. every 2 cycles, and the PCR mixture was finally treated at 72° C. for 8 minutes, and stored at 4° C.

Figure 3:
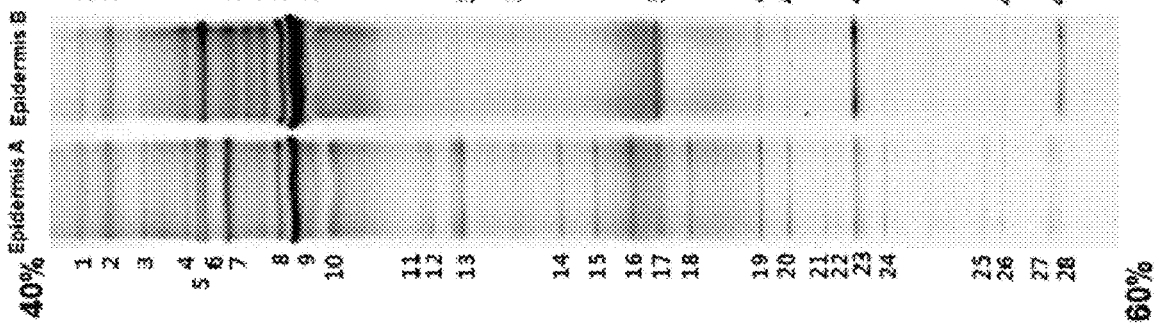
FIG. 3 is a diagram showing changes in skin flora according to EPI-7 treatment.

Thereafter, the resulting PCR product was used in denaturing gradient gel electrophoresis (DGGE) analysis. In the DGGE analysis, a D-code system (Bio-rad, USA) was used. A concentration of a polyacrylamide gel used was 8%, and 40% polyacrylamide bis-solution (29:1, 3.3% C) (Bio-Rad, USA) was used to prepare a gel with a vertical concentration gradient of 40-60%. At this time, 7 M urea and 40% (w/v) formamide (Sigma, USA) were used as a denaturant. The D-code system was filled with about 7 L of TAE buffer (20 mM Tris, 10 mM acetic acid, 0.5 mM EDTA, pH 8.0), and equal amounts of 2x loading dye (0.05% bromophenol blue, 0.05% xylene cyanol, 70% glycerol) and the PCR product were mixed and electrophoresed at 50 V for 800 minutes. The electrophoresed polyacrylamide gel was stained with a Redsafe (Intron, Korea) solution for 15 minutes, and specific bands which appeared were analyzed. Results are shown in FIG. 3. Further, images of DGGE bands were quantified and analyzed using GelCompar2 (Bionumeric, Belgium) to generate a histogram. For sequencing analysis, the DGGE gel bands were sent to Macrogen Inc., and results are shown in FIG. 4.

As shown in FIGS. 3 and 4, a decreased number of bands and strong expression of particular bands were observed in Epidermis B (after treatment of the culture), as compared to Epidermis A (before treatment of the culture).

The increased expression of bands indicates an increase in population. Most of the DGGE bands with increased intensity indicated microorganisms of the genus *staphylococcus*, which belong to skin flora symbiotic with the skin and effective in strengthening the skin barrier and moisturizing the skin.

These results suggest that EPI-7 influences strengthening of the skin barrier and moisturizing of the skin by increasing the microorganisms.

3.2. Analysis of Skin Wound Healing, Skin Barrier Strengthening, and Moisturizing Activities In order to analyze skin wound healing, skin barrier strengthening, and moisturizing activities, expression levels of filaggrin, hyaluronic acid synthase3 (HAS3), claudin 1, claudin 4, αSMase, aquaporin 3 (AQP3) transglutaminase 1, and CerS3, which are skin barrier strengthening and moisturizing activity-related factors, in a human keratinocyte cell line (HaCaT) were examined, according to EPI-7 treatment, by RT-PCR.

In detail, HaCaT cells, which are human keratinocytes, were cultured in 10% fetal bovine serum-containing DMEM (Dulbecco's modified Eagle's Medium, Gibco 1210-0038), and culturing was carried out in an incubator at 37° C. and 5% CO2. The cultured cell line was treated with 1 mM retinol as a positive control group. As another positive control group, 20 ml of the cell culture was treated with cultures of *Bifidobacterium animalis* (UB) and *Lactobacillus acidophilus* (AB) at a concentration of 1%. Further, EPI-7 cultures were treated at a concentration of 0.1%, 0.5%, or 1.0%.

Thereafter, HaCaT cells were further incubated for 24 hours, and recovered, and 1 ml of trizol (RNAiso, DAKARA, Japan) was added thereto to isolate RNA. Further, for RT-PCR, RNA was quantified by using a Nanodrop 2000 (Thermo, USA), and reacted at 42° C. for 55 minutes and at 70° C. for 15 minutes to synthesize cDNA (Reverse Transcriptase Mix, ELPIS biotech, Korea). RT-PCR was performed by using Step One Plus (Applied Biosystems, USA), and SYBR Green supermix (Applied Biosystems, USA) was added together with primers and cDNA. Polymerase was activated at 94° C. for 5 minutes and then polymerization was performed at 95° C. for 30 seconds, at 54° C. for 1 minute, and at 72° C. for 1 minute, for 40 cycles.

Primers of SEQ ID NOS: 7 and 8 were used for filaggrin, primers of SEQ ID NOS: 9 and 10 for HAS3, primers of SEQ ID NOS: 11 and 12 for claudin 1, primers of SEQ ID NOS: 13 and 14 for claudin 4, primers of SEQ ID NOS: 15 and 16 for αSMase, primers of SEQ ID NOS: 17 and 18 for AQP3, primers of SEQ ID NOS: 19 and 20 for transglutaminase 1, primers of SEQ ID NOS: 21 and 22 for CerS3, and primers of SEQ ID NOS: 23 and 24 for beta-actin.

Figure 5:
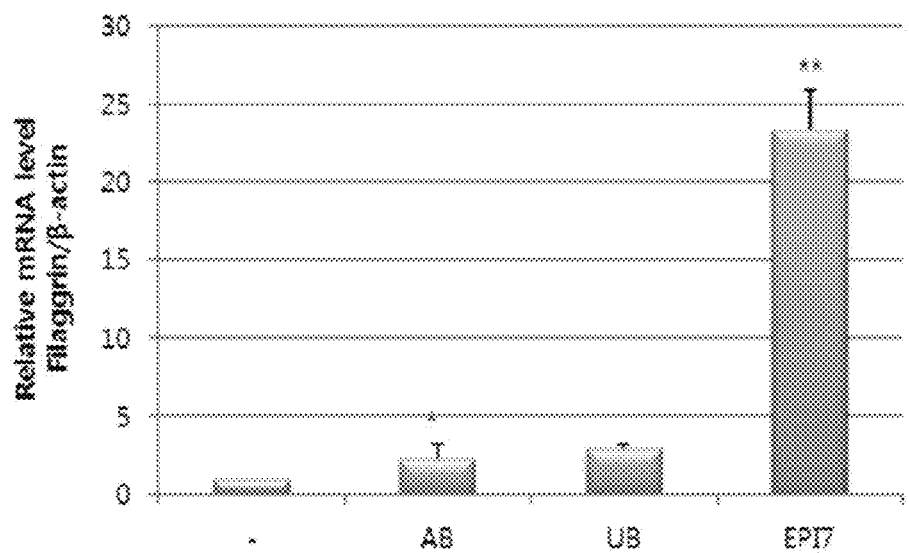
FIG. 5 is a graph showing a comparison of effects of EPI-7 on filaggrin expression in human keratinocytes and a positive control group.

FIG. 5 is a graph showing a comparison of the effect of EPI-7 on filaggrin expression in human keratinocytes and a positive control group.

Figure 6:
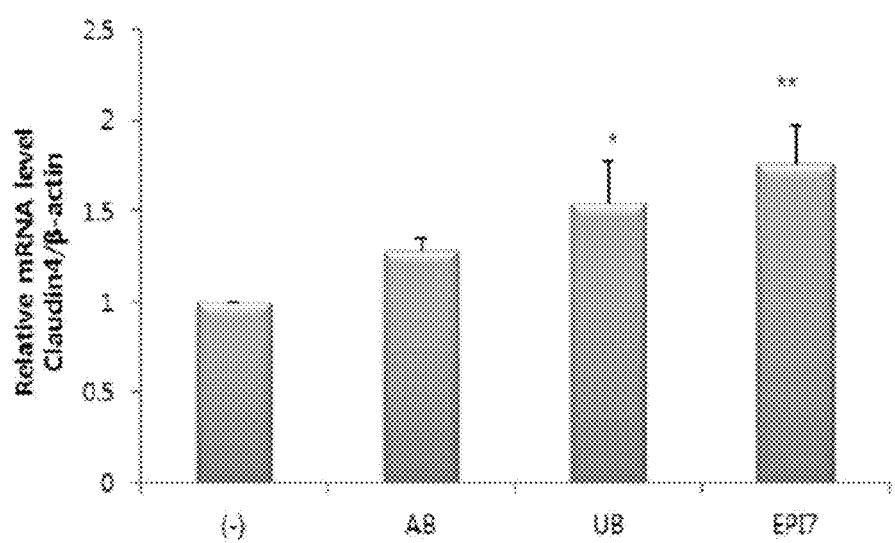
FIG. 6 is a graph showing a comparison of effects of EPI-7 on claudin 4 expression in human keratinocytes and a positive control group.

FIG. 6 is a graph showing a comparison of the effect of EPI-7 on claudin 4 expression in human keratinocytes and a positive control group.

Figure 7:
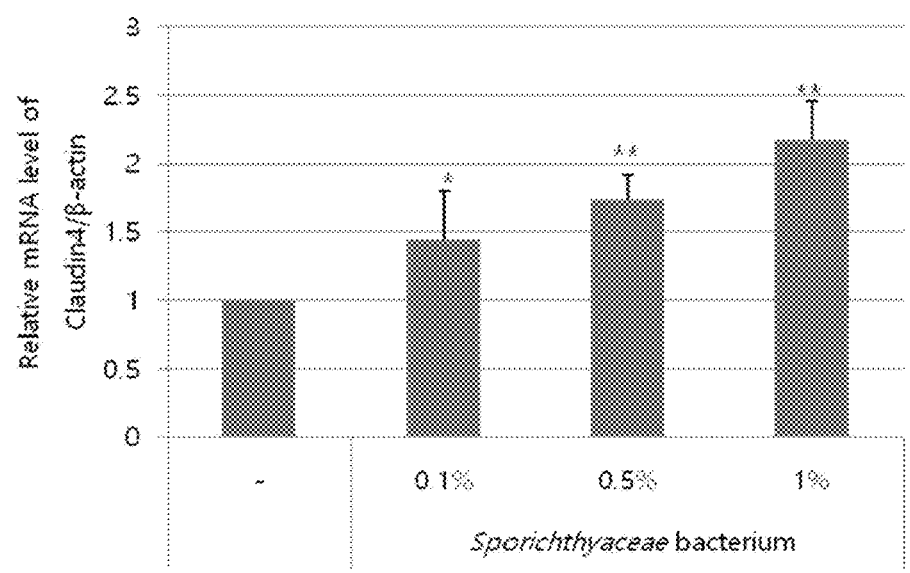
FIG. 7 is a graph showing effects of different doses of EPI-7 on claudin 4 expression in human keratinocytes.

FIG. 7 is a graph showing the effects of different doses of EPI-7 on claudin 4 expression in human keratinocytes.

Figure 8:
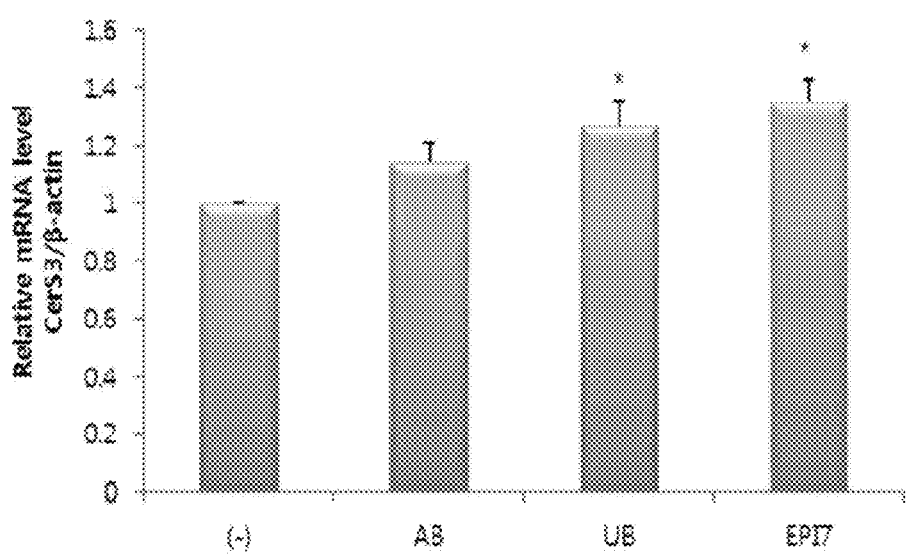
FIG. 8 is a graph showing a comparison of effects of EPI-7 on CerS3 expression in human keratinocytes and a positive control group.

FIG. 8 is a graph showing a comparison of the effect of EPI-7 on CerS3 expression in human keratinocytes and a positive control group.

Figure 9:
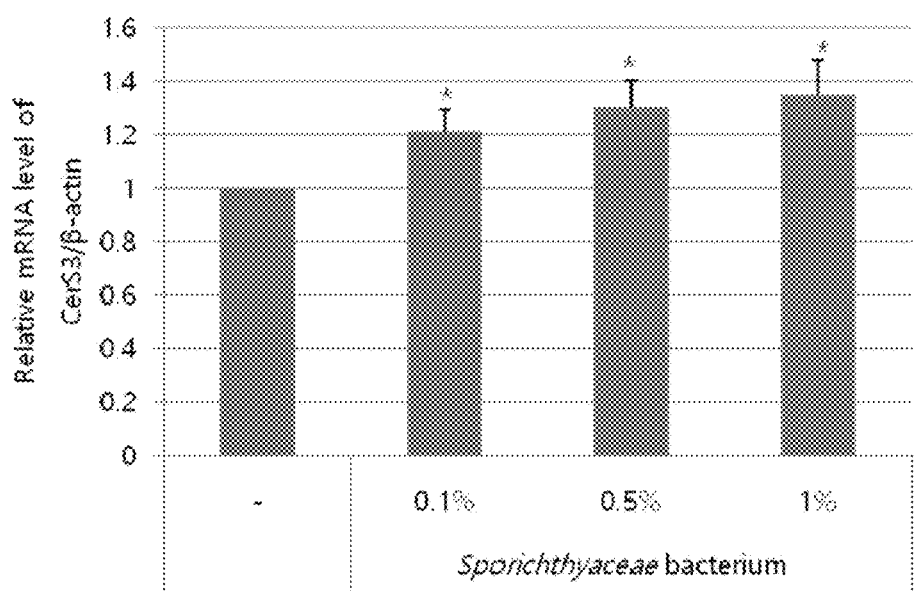
FIG. 9 is a graph showing effects of different doses of EPI-7 on CerS3 expression in human keratinocytes.

FIG. 9 is a graph showing the effects of different doses of EPI-7 on CerS3 expression in human keratinocytes.

Figure 10:
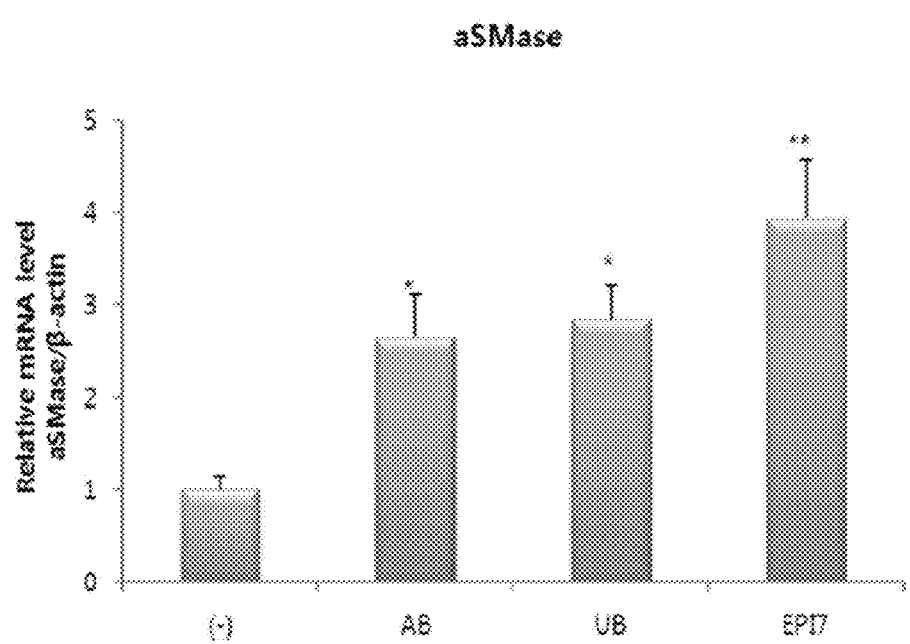
FIG. 10 is a graph showing a comparison of effects of EPI-7 on αSMase expression in human keratinocytes and a positive control group.

FIG. 10 is a graph showing a comparison of the effect of EPI-7 on αSMase expression in human keratinocytes and a positive control group.

Figure 11:
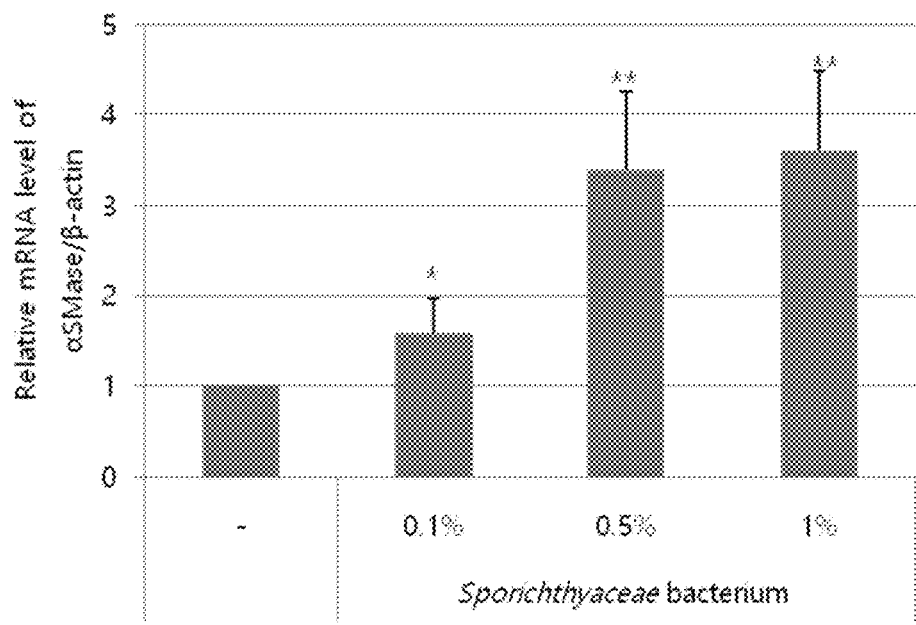
FIG. 11 is a graph showing effects of different doses of EPI-7 on αSMase expression in human keratinocytes.

FIG. 11 is a graph showing the effects of different doses of EPI-7 on αSMase expression in human keratinocytes.

Figure 12:
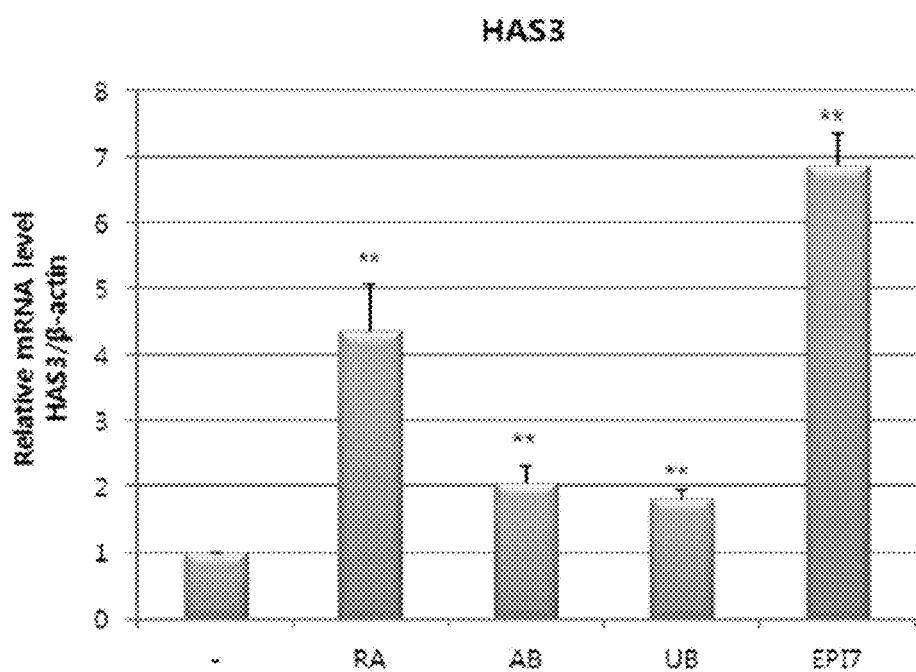
FIG. 12 is a graph showing a comparison of effects of EPI-7 on HAS expression in human keratinocytes and a positive control group.

FIG. 12 is a graph showing a comparison of the effect of EPI-7 on HAS expression in human keratinocytes and a positive control group.

Figure 13:
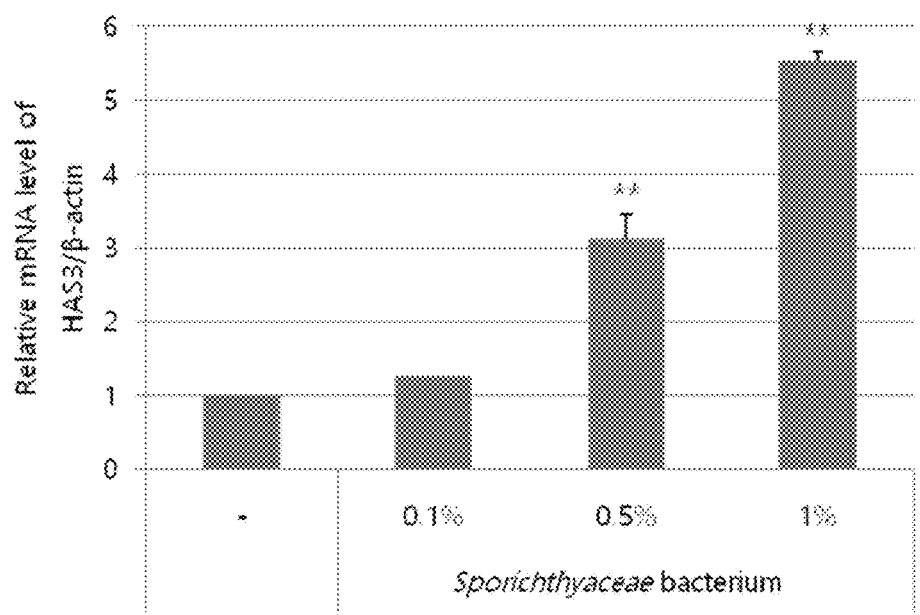
FIG. 13 is a graph showing effects of different doses of EPI-7 on HAS expression in human keratinocytes.

FIG. 13 is a graph showing the effects of different doses of EPI-7 on HAS expression in human keratinocytes.

Figure 14:
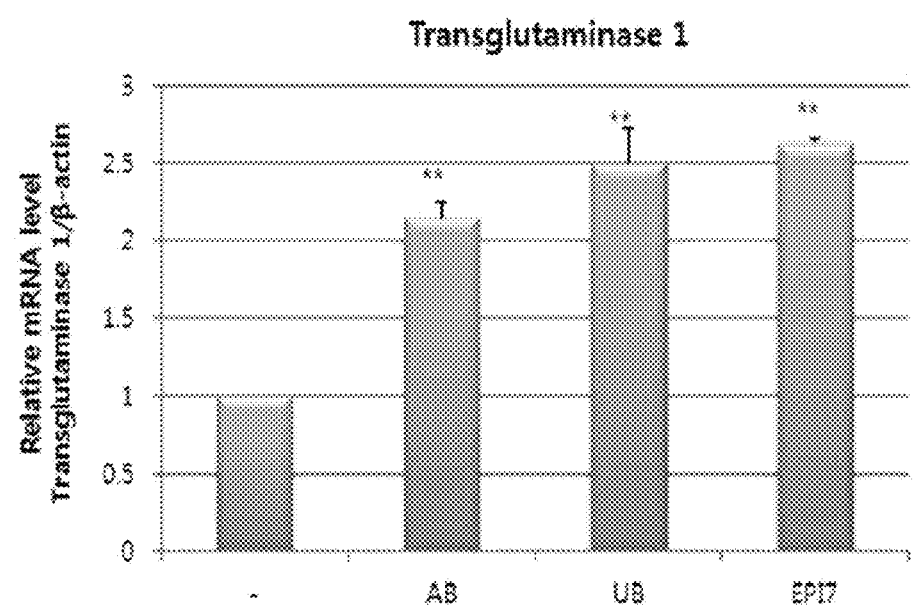
FIG. 14 is a graph showing a comparison of effects of EPI-7 on transglutaminase 1 expression in human keratinocytes and a positive control group.

FIG. 14 is a graph showing a comparison of the effect of EPI-7 on transglutaminase 1 expression in human keratinocytes and a positive control group.

Figure 15:
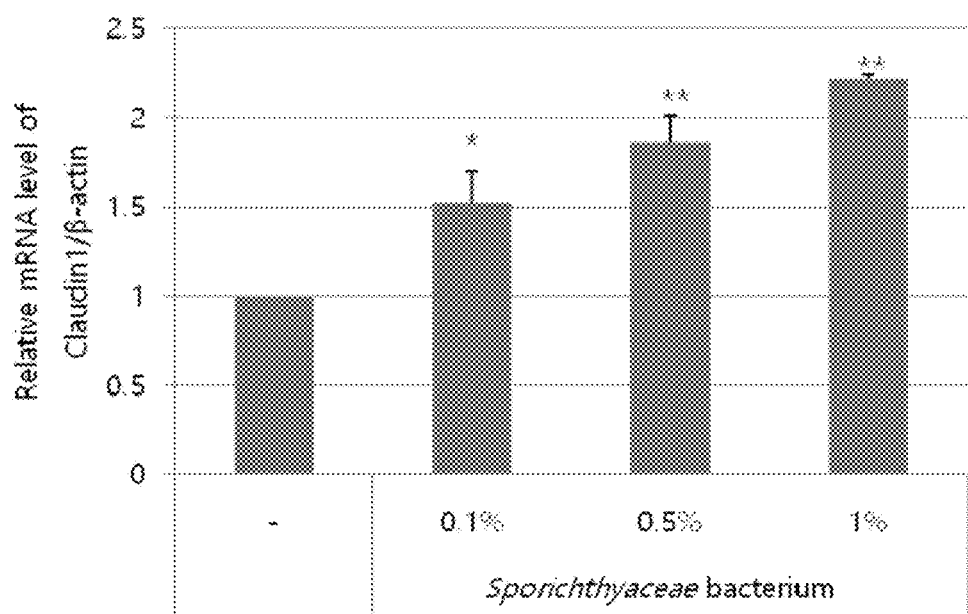
FIG. 15 is a graph showing effects of different doses of EPI-7 on claudin 1 expression in human keratinocytes.

FIG. 15 is a graph showing the effects of different doses of EPI-7 on claudin 1 expression in human keratinocytes.

Figure 16:
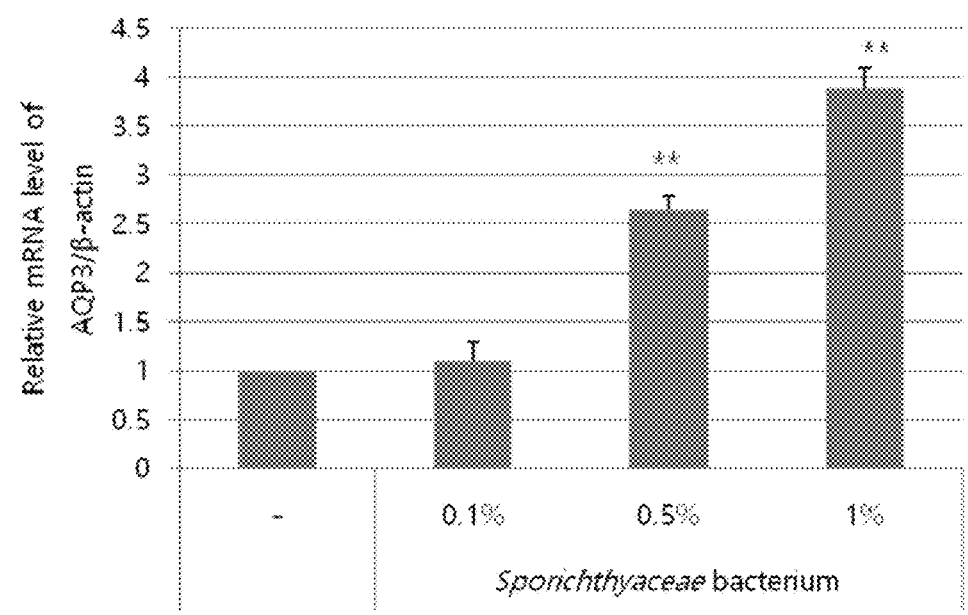
FIG. 16 is a graph showing effects of different doses of EPI-7 on aquaporin 3 expression in human keratinocytes.

FIG. 16 is a graph showing the effects of different doses of EPI-7 on aquaporin 3 expression in human keratinocytes.

As shown in FIG. 5, EPI-7 was found to significantly increase expression of filaggrin which is a keratinocyte differentiation marker and a precursor protein of a natural moisturizing factor responsible for moisturizing the skin surface.

As shown in FIGS. 6, 7, and 15, EPI-7 was found to significantly increase expression of claudin 1 and 4, which are tight junction structures responsible for protecting the internal organs from the external environment and maintaining homeostasis of the human body.

As shown in FIGS. 8 and 11, EPI-7 was found to significantly increase expression of CerS3 and αSMase, which are enzymes essential for ceramide synthesis.

As shown in FIGS. 12 and 13, EPI-7 was found to significantly increase expression of HAS3, which is responsible for synthesis of hyaluronic acid which is an extracellular matrix component maintaining skin moisture, and showed higher efficacy than the positive control, retinol.

As shown in FIG. 14, EPI-7 was found to significantly increase expression of transglutaminase 1, which plays a critical role in forming cornified envelopes.

As shown in FIG. 16, EPI-7 was found to significantly increase expression of AQP3, which plays a role in providing water for the human skin, functions as a water channel to facilitate cell migration, and functions as a glycerol transporter to regulate keratinocyte proliferation and differentiation, thereby treating wounds.

Taken together, it can be seen that EPI-7 enhances the flexibility and firmness of the skin, improves the skin's water retention ability so as to exhibit a skin moisturizing effect, strengthens the skin barrier function by more effectively controlling intercellular adhesion and migration of water-containing solutes and water through the periplasmic space, and increases proliferation, differentiation, and migration of keratinocytes to exhibit a significant effect on wound healing.

3.3. Analysis of Anti-Inflammatory Activity in Skin

In order to analyze anti-inflammatory activity of EPI-7, HaCaT cells were treated with *Staphylococcus aureus* (*S. aureus*), which is an inflammation inducer, and *S. epidermidis* and EPI-7 were co-cultured with human HaCaT cells, and then mRNA expression levels of inflammatory factors were assessed.

In detail, HaCaT cells were cultured and seeded on a 6-well plate. 24 hours later, a micromembrane well was placed on the top of a cell single layer, and then living cells (SA: *S. aureus*, SA_SE: *S. aureus*+*S. epidermidis*, SA_EPI-7: *S. aureus*+EPI-7) were seeded at a cell density of $1.0 \times 10^{14}$.

The cells were further co-cultured for 24 hours, and then the cells and medium were removed. RT-PCR was performed in the same manner as in Example 3.2., except that a combination of SEQ ID NOS: 25 and 26, a combination of SEQ ID NOS: 27 and 28, a combination of SEQ ID NOS: 29 and 30, and a combination of SEQ ID NOS: 31 and 32 were used as primers for TNF-α, IL-1a, TSLP, and DDIT3, respectively. Results are shown in FIG. 17.

Figure 17:
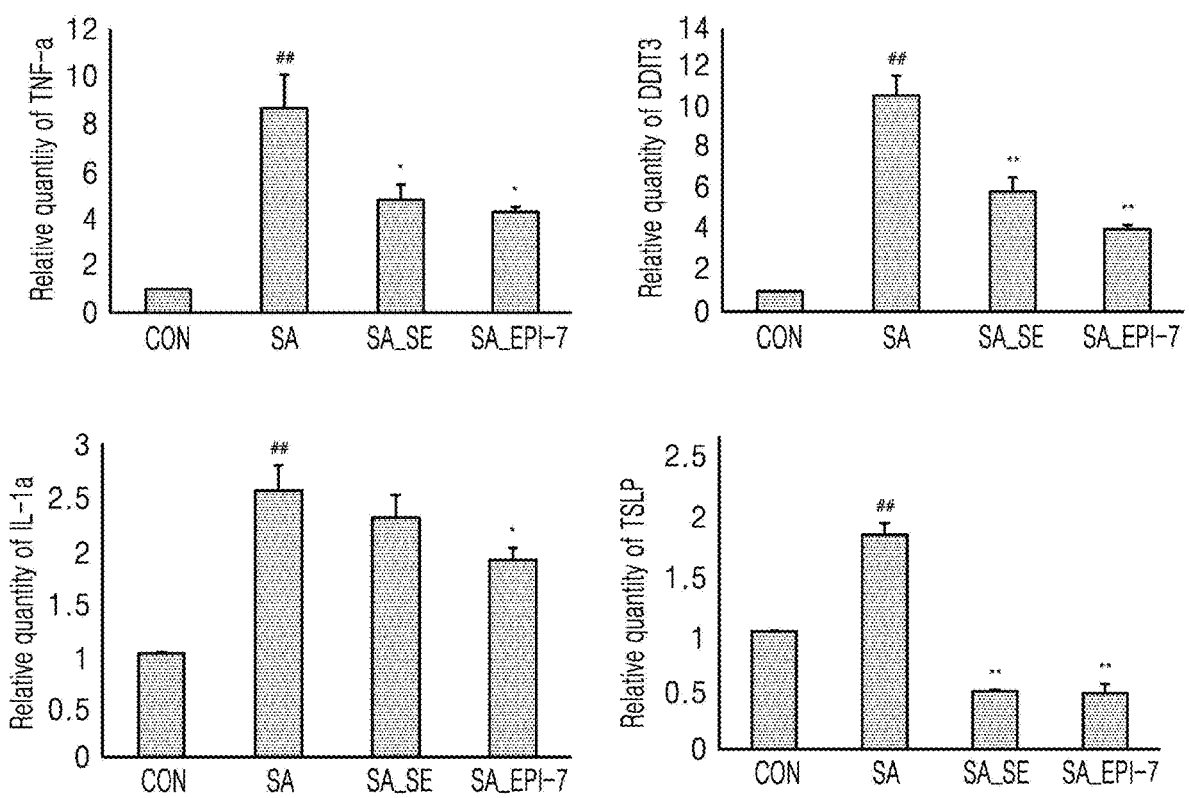
FIG. 17 shows graphs showing effects of EPI-7 on inflammatory factors.

FIG. 17 is a graph showing effects of EPI-7 on inflammatory factors.

As shown in FIG. 7, EPI-7 was found to significantly inhibit expression of TNF-α, IL-1a, TSLP, and DDIT3, which are skin inflammatory factors. This result suggests that EPI-7 and the culture thereof may be used for skin inflammation-related diseases.

3.4. Analysis of Antipruritic Activity in Skin

In order to analyze antipruritic activity of EPI-7, mRNA expression levels of TSLP (Thymic stromal lymphopoietin) and TARC (Thymus and activation-regulated chemokine), which are pruritic factors, were assessed. In detail, HaCaT cells were treated with polyinosinic:polycytidylic acid (Poly I:C), which is a synthetic ribonucleic acid that induces interferon production, and then cultured for 24 hours to stimulate HaCaT cells. Aged cells by stimulation were treated with the EPI-7 culture at a concentration of 0.1%, 0.5%, or 1.0%, and further cultured for 24 hours. RT-PCR was performed in the same manner as in Example 3.3., except that a combination of SEQ ID NOS: 33 and 34 was used as TARC primers.

Figure 18:
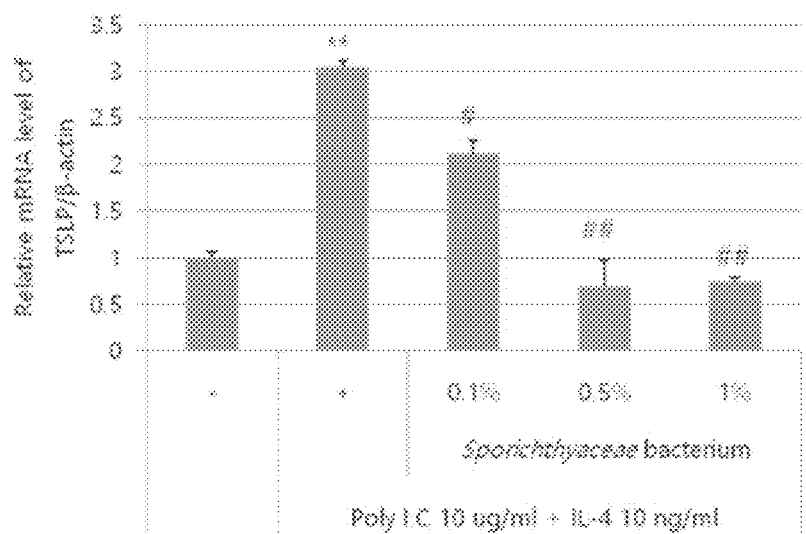
FIG. 18 is a graph showing effects of different doses of EPI-7 on TSLP expression in human keratinocytes.
Figure 19:
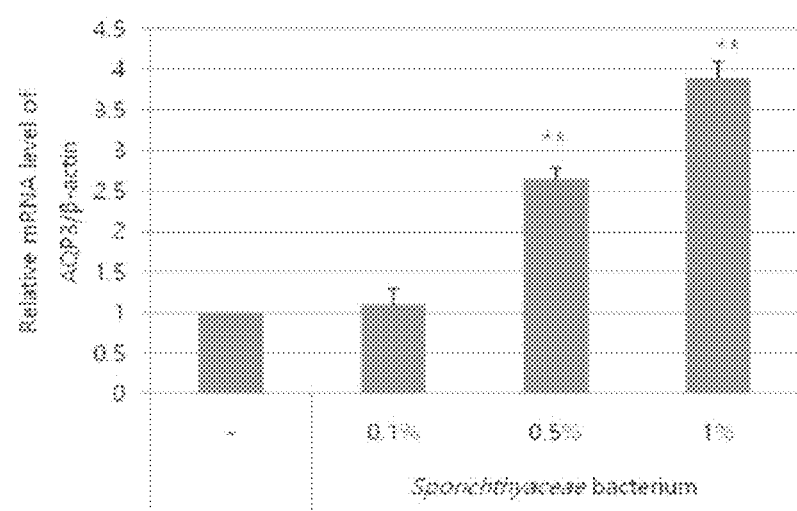
FIG. 19 is a graph showing effects of different doses of EPI-7 on TARC expression in human keratinocytes.

Results are shown in FIGS. 18 and 19.

FIG. 18 is a graph showing the effects of different doses of EPI-7 on TSLP expression in human keratinocytes.

FIG. 19 is a graph showing the effects of different doses of EPI-7 on TARC expression in human keratinocytes.

As shown in FIGS. 18 and 19, EPI-7 was found to significantly decrease expression of TSLP and TARC, which are pruritic factors. This result suggests that EPI-7 and the culture thereof may be used for skin inflammation-related diseases and pruritus.

3.5. Analysis of Cytotoxicity

In order to examine cytotoxicity of EPI-7, an MTT assay was performed.

In detail, HaCaT cells were prepared in the same manner as in Example 3.1., and dispensed in a 96-well plate at a density of $3 \times 10^4$ cells/well. 24 hours later, a FBS-free medium was replaced. An EPI-7 culture was diluted with the FBS-free medium at concentrations of 0.01%, 0.1%, 1%, 10%, and 50%, and used to treat the cells. After incubation for 24 hours, the medium was removed, and 0.5 μg/mL of MTT (Sigma-Aldrich, St. Louis, Mo.) reagent was added to crystallize the cells, followed by further incubation for 4 hours. After removing the MTT reagent, crystals were dissolved in dimethyl sulfoxide (DMSO, Sigma-Aldrich, St. Louis, Mo.). Absorbance at 540 nm was measured, and compared with a non-treatment group to measure cell viability. Results are shown in FIG. 20.

Figure 20:
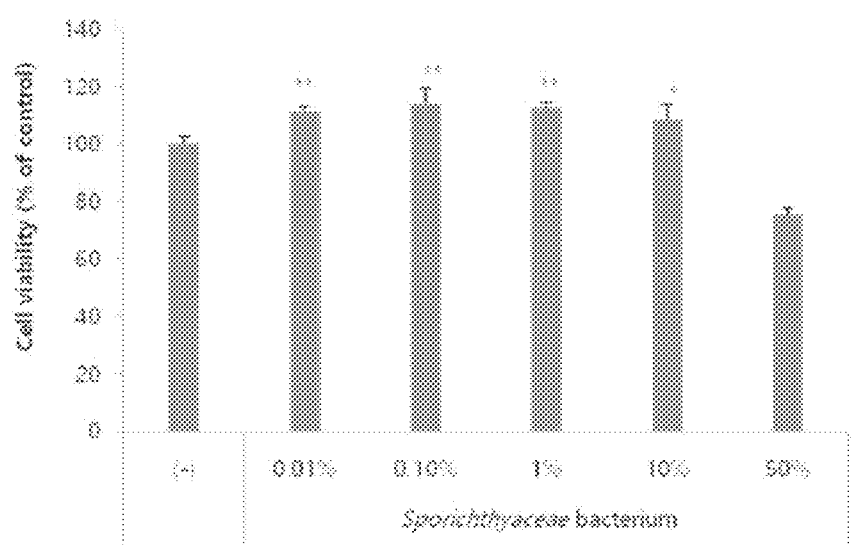
FIG. 20 is a graph showing effects of EPI-7 on cell viability.

FIG. 20 is a graph showing the effect of EPI-7 on cell viability.

As shown in FIG. 20, EPI-7 was found to have no cytotoxicity even at high concentrations.

Figure 21:
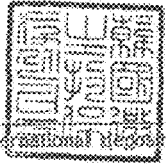
FIG. 21 is a copy of Budapest Treaty on the International Recognition of the Deposit of Microorganisms for the Purpose of Patent Procedure.

FIG. 21 is a copy of Budapest Treaty on the International Recognition of the Deposit of Microorganisms for the Purpose of Patent Procedure.

The invention claimed is:

1. A method of preventing, improving, or treating a skin disease or inflammatory diseases of a subject, the method comprising administering a microorganism of the genus *Epidermidibacterium*, wherein the microorganism is deposited under Accession NO. KCCM 11843P of the species *Epidermidibacterium keratini* (*Epidermidibacterium keratini* sp.) or a culture thereof to a subject in need thereof.

2. The method of claim 1, wherein the skin diseases are any one or more selected from the group consisting of a skin wound, dermatitis, atopic dermatitis, pruritus, eczematous dermatosis, dry eczema, erythema, urticaria, psoriasis, drug rash, and acne.

3. The method of claim 1, wherein the inflammatory diseases are one or more selected from the group consisting of dermatitis, allergy, atopy, conjunctivitis, periodontitis, rhinitis, otitis media, sore throat, tonsillitis, pneumonia, gastric ulcer, gastritis, Crohn's disease, colitis, arthritis, ankylosing spondylitis, tendinitis, tenosynovitis, peritendinitis, myositis, hepatitis, cystitis, and nephritis.

* * * * *

SEQUENCE LISTING

```
<160> NUMBER OF SEQ ID NOS: 34

<210> SEQ ID NO 1
<211> LENGTH: 1450
<212> TYPE: DNA
```

<213> ORGANISM: Epidermidibacterium keratini

<400> SEQUENCE: 1

| | |
|---|---|
| caggacgaac gctggcggcg tgcttaacac atgcaagtcg agcgaagctc tcctcttcgg | 60 |
| aggagatgac ttagcggcga acgggtgagt aacacgtggg caacctgccc ttagctctgg | 120 |
| gataagcgat ggaaacgtcg tctaataccg gatacgacac ggaacggcat cattaccgtg | 180 |
| tggaaagaat ttcggctaag gatgggcccg cggcctatca gcttgttggt ggggtaatgg | 240 |
| cctaccaagg cttcgacggg taaccggcct gagagggcga ccggtcacac tgggactgag | 300 |
| acacggccca gactcctacg ggaggcagca gtggggaata ttgcacaatg ggcgaaagcc | 360 |
| tgatgcagcg acgccgcgtg agggatgacg gccttcgggt tgtaaacctc tttcagcagg | 420 |
| gacgaagcga agtgacggt acctgcagaa gaagcgccgg ccaactacgt gccagcagcc | 480 |
| gcggtaatac gtagggcgca agcgttgtcc ggaattattg ggcgtaaaga gctcgtaggc | 540 |
| ggtttatcac gtcggctgtg aaatcccgag gcttaacctc gggcctgcag tcgatacggg | 600 |
| ttgactagag tgaagcaggg gagactggaa ttcctggtgt agcggtgaaa tgcgcagata | 660 |
| tcaggaggaa caccggtggc gaaggcgggt ctctgggctt taactgacgc tgaggagcga | 720 |
| aagcgtgggt agcgaacagg attagatacc ctggtagtcc acgccgtaaa cggtgggcgc | 780 |
| taggtgtggg gaccattcca cggtctccgt gccgcagcta acgcattaag cgccccgcct | 840 |
| ggggagtacg gccgcaaggc taaaactcaa aggaattgac gggggcccgc acaagcggcg | 900 |
| gagtatgttg cttaattcga tgcaacgcga agaaccttac caaggcttga catataccga | 960 |
| aaactcatag agatatgagg tccttttggg cggtatacag gtggtgcatg gttgtcgtca | 1020 |
| gctcgtgtcg tgagatgttg ggttaagtcc cgcaacgagc gcaaccctcg ttctatgttg | 1080 |
| ccagcacgta atggtgggga ctcataggag actgccgggg tcaactcgga ggaaggtggg | 1140 |
| gatgacgtca aatcatcatg ccccttatgt cttgggctgc aaacatacta caatggccgg | 1200 |
| tacaaagggc tgcgataccg taaggtggag cgaatcccaa aaagccggtc tcagttcgga | 1260 |
| ttggggtctg caactcgacc ccatgaagtc ggagtcgcta gtaatcgcag atcagcaacg | 1320 |
| ctgcggtgaa tacgttcccg ggccttgtac acaccgcccg tcaagtcatg aaagtcggta | 1380 |
| acacccgaag ccggtggcct aacctttttg gagggagccg tcgaaggtgg gactggcgat | 1440 |
| taggactaag | 1450 |

<210> SEQ ID NO 2
<211> LENGTH: 20
<212> TYPE: DNA
<213> ORGANISM: Artificial Sequence
<220> FEATURE:
<223> OTHER INFORMATION: primer for bacteria

<400> SEQUENCE: 2

| | |
|---|---|
| agagtttgat cmtggctcag | 20 |

<210> SEQ ID NO 3
<211> LENGTH: 22
<212> TYPE: DNA
<213> ORGANISM: Artificial Sequence
<220> FEATURE:
<223> OTHER INFORMATION: primer for bacteria

<400> SEQUENCE: 3

| | |
|---|---|
| tacggytacc ttgttacgac tt | 22 |

```
<210> SEQ ID NO 4
<211> LENGTH: 40
<212> TYPE: DNA
<213> ORGANISM: Artificial Sequence
<220> FEATURE:
<223> OTHER INFORMATION: GC clamp for amplification of 16s ribosomal DNA
      gene

<400> SEQUENCE: 4
cgcccggggc gcgccccggg cggggcgggg gcacggggg                            40

<210> SEQ ID NO 5
<211> LENGTH: 17
<212> TYPE: DNA
<213> ORGANISM: Artificial Sequence
<220> FEATURE:
<223> OTHER INFORMATION: forward primer for amplification of 16s
      ribosomal DNA gene

<400> SEQUENCE: 5
cctacgggag gcagcag                                                   17

<210> SEQ ID NO 6
<211> LENGTH: 17
<212> TYPE: DNA
<213> ORGANISM: Artificial Sequence
<220> FEATURE:
<223> OTHER INFORMATION: reverse primer for amplification of 16s
      ribosomal DNA gene

<400> SEQUENCE: 6
attaccgcgg ctgctgg                                                   17

<210> SEQ ID NO 7
<211> LENGTH: 21
<212> TYPE: DNA
<213> ORGANISM: Artificial Sequence
<220> FEATURE:
<223> OTHER INFORMATION: forward primer for filaggrin

<400> SEQUENCE: 7
agtgcactca gggggctcac a                                              21

<210> SEQ ID NO 8
<211> LENGTH: 20
<212> TYPE: DNA
<213> ORGANISM: Artificial Sequence
<220> FEATURE:
<223> OTHER INFORMATION: reverse primer for filaggrin

<400> SEQUENCE: 8
ccggcttggc cgtaatgtgt                                                20

<210> SEQ ID NO 9
<211> LENGTH: 20
<212> TYPE: DNA
<213> ORGANISM: Artificial Sequence
<220> FEATURE:
<223> OTHER INFORMATION: forward primer for HAS3

<400> SEQUENCE: 9
cttaagggtt gcttgcttgc                                                20

<210> SEQ ID NO 10
<211> LENGTH: 20
<212> TYPE: DNA
<213> ORGANISM: Artificial Sequence
```

<220> FEATURE:
<223> OTHER INFORMATION: reverse primer for HAS3

<400> SEQUENCE: 10
gttcgtggga gatgaaggaa                                         20

<210> SEQ ID NO 11
<211> LENGTH: 33
<212> TYPE: DNA
<213> ORGANISM: Artificial Sequence
<220> FEATURE:
<223> OTHER INFORMATION: forward primer for claudin 1

<400> SEQUENCE: 11
gctctagaat tctcacacgt agtctttccc gct                          33

<210> SEQ ID NO 12
<211> LENGTH: 33
<212> TYPE: DNA
<213> ORGANISM: Artificial Sequence
<220> FEATURE:
<223> OTHER INFORMATION: reverse primer for claudin 1

<400> SEQUENCE: 12
gctctagaat tctcacacgt agtctttccc gct                          33

<210> SEQ ID NO 13
<211> LENGTH: 33
<212> TYPE: DNA
<213> ORGANISM: Artificial Sequence
<220> FEATURE:
<223> OTHER INFORMATION: forward primer for claudin 4

<400> SEQUENCE: 13
gctctagaat tccgagcgag tcatggccaa cgc                          33

<210> SEQ ID NO 14
<211> LENGTH: 33
<212> TYPE: DNA
<213> ORGANISM: Artificial Sequence
<220> FEATURE:
<223> OTHER INFORMATION: reverse primer for claudin 4

<400> SEQUENCE: 14
gctctagaat tctcacacgt agtctttccc gct                          33

<210> SEQ ID NO 15
<211> LENGTH: 23
<212> TYPE: DNA
<213> ORGANISM: Artificial Sequence
<220> FEATURE:
<223> OTHER INFORMATION: forward primer for aSMase

<400> SEQUENCE: 15
actttgataa ctgctcctct gac                                     23

<210> SEQ ID NO 16
<211> LENGTH: 20
<212> TYPE: DNA
<213> ORGANISM: Artificial Sequence
<220> FEATURE:
<223> OTHER INFORMATION: reverse primer for aSMase

<400> SEQUENCE: 16
ttcgtgtcca gcagagtacc                                         20

```
<210> SEQ ID NO 17
<211> LENGTH: 20
<212> TYPE: DNA
<213> ORGANISM: Artificial Sequence
<220> FEATURE:
<223> OTHER INFORMATION: forward primer for AQP3

<400> SEQUENCE: 17
agacagcccc ttcaggattt                                              20

<210> SEQ ID NO 18
<211> LENGTH: 20
<212> TYPE: DNA
<213> ORGANISM: Artificial Sequence
<220> FEATURE:
<223> OTHER INFORMATION: reverse primer for AQP3

<400> SEQUENCE: 18
tcccttgccc tgaatatctg                                              20

<210> SEQ ID NO 19
<211> LENGTH: 20
<212> TYPE: DNA
<213> ORGANISM: Artificial Sequence
<220> FEATURE:
<223> OTHER INFORMATION: forward primer for TG1

<400> SEQUENCE: 19
ccccaagaga ctagcagtgg                                              20

<210> SEQ ID NO 20
<211> LENGTH: 20
<212> TYPE: DNA
<213> ORGANISM: Artificial Sequence
<220> FEATURE:
<223> OTHER INFORMATION: reverse primer for TG1

<400> SEQUENCE: 20
agaccaggcc attcttgatg                                              20

<210> SEQ ID NO 21
<211> LENGTH: 22
<212> TYPE: DNA
<213> ORGANISM: Artificial Sequence
<220> FEATURE:
<223> OTHER INFORMATION: forward primer for CerS3

<400> SEQUENCE: 21
acattccaca aggcaaccat tg                                           22

<210> SEQ ID NO 22
<211> LENGTH: 20
<212> TYPE: DNA
<213> ORGANISM: Artificial Sequence
<220> FEATURE:
<223> OTHER INFORMATION: reverse primer for CerS3

<400> SEQUENCE: 22
ctcttgattc cgccgactcc                                              20

<210> SEQ ID NO 23
<211> LENGTH: 20
<212> TYPE: DNA
<213> ORGANISM: Artificial Sequence
<220> FEATURE:
<223> OTHER INFORMATION: forward primer for b-actin
```

```
<400> SEQUENCE: 23
ggccatctct tgctcgaagt                                              20

<210> SEQ ID NO 24
<211> LENGTH: 20
<212> TYPE: DNA
<213> ORGANISM: Artificial Sequence
<220> FEATURE:
<223> OTHER INFORMATION: reverse primer for b-actin

<400> SEQUENCE: 24
gacaccttca acaccccagc                                              20

<210> SEQ ID NO 25
<211> LENGTH: 20
<212> TYPE: DNA
<213> ORGANISM: Artificial Sequence
<220> FEATURE:
<223> OTHER INFORMATION: forward primer for TNF-a

<400> SEQUENCE: 25
cttctccttc ctgatcgtgg                                              20

<210> SEQ ID NO 26
<211> LENGTH: 21
<212> TYPE: DNA
<213> ORGANISM: Artificial Sequence
<220> FEATURE:
<223> OTHER INFORMATION: reverse primer for TNF-a

<400> SEQUENCE: 26
gctggttatc tctcagctcc a                                            21

<210> SEQ ID NO 27
<211> LENGTH: 24
<212> TYPE: DNA
<213> ORGANISM: Artificial Sequence
<220> FEATURE:
<223> OTHER INFORMATION: forward primer for IL-1a

<400> SEQUENCE: 27
tggctcattt tccctcaaaa gttg                                         24

<210> SEQ ID NO 28
<211> LENGTH: 25
<212> TYPE: DNA
<213> ORGANISM: Artificial Sequence
<220> FEATURE:
<223> OTHER INFORMATION: reverse primer for IL-1a

<400> SEQUENCE: 28
agaaatcgtg aaatccgaag tcaag                                        25

<210> SEQ ID NO 29
<211> LENGTH: 21
<212> TYPE: DNA
<213> ORGANISM: Artificial Sequence
<220> FEATURE:
<223> OTHER INFORMATION: forward primer for TSLP

<400> SEQUENCE: 29
gctatctggt gcccaggcta t                                            21

<210> SEQ ID NO 30
```

-continued

```
<211> LENGTH: 21
<212> TYPE: DNA
<213> ORGANISM: Artificial Sequence
<220> FEATURE:
<223> OTHER INFORMATION: reverse primer for TSLP

<400> SEQUENCE: 30
cgacgccaca atccttgtaa t                                              21

<210> SEQ ID NO 31
<211> LENGTH: 20
<212> TYPE: DNA
<213> ORGANISM: Artificial Sequence
<220> FEATURE:
<223> OTHER INFORMATION: forward primer for DDIT3

<400> SEQUENCE: 31
tgcctttctc ttcggacact                                                20

<210> SEQ ID NO 32
<211> LENGTH: 20
<212> TYPE: DNA
<213> ORGANISM: Artificial Sequence
<220> FEATURE:
<223> OTHER INFORMATION: reverse primer for DDIT3

<400> SEQUENCE: 32
tgtgacctct gctggttctg                                                20

<210> SEQ ID NO 33
<211> LENGTH: 18
<212> TYPE: DNA
<213> ORGANISM: Artificial Sequence
<220> FEATURE:
<223> OTHER INFORMATION: forward primer for TARC

<400> SEQUENCE: 33
cttctctgca gcacatcc                                                  18

<210> SEQ ID NO 34
<211> LENGTH: 19
<212> TYPE: DNA
<213> ORGANISM: Artificial Sequence
<220> FEATURE:
<223> OTHER INFORMATION: reverse primer for TARC

<400> SEQUENCE: 34
aagacctctc aaggctttg                                                 19
```